(12) United States Patent  
Silderhuis

(10) Patent No.: US 8,997,515 B2  
(45) Date of Patent: Apr. 7, 2015

(54) AUXILIARY DEVICE INTENDED FOR ADDING TO AN AIR CONDITIONING DEVICE

(75) Inventor: Hermannus Gerhardus Maria Silderhuis, Enschede (NL)

(73) Assignee: Virobuster GmbH (DE)

( * ) Notice: Subject to any disclaimer, the term of this patent is extended or adjusted under 35 U.S.C. 154(b) by 1210 days.

(21) Appl. No.: 12/090,205

(22) PCT Filed: Oct. 12, 2006

(86) PCT No.: PCT/NL2006/050258  
§ 371 (c)(1),  
(2), (4) Date: Aug. 7, 2008

(87) PCT Pub. No.: WO2007/086726  
PCT Pub. Date: Aug. 2, 2007

(65) Prior Publication Data  
US 2009/0217690 A1    Sep. 3, 2009

(30) Foreign Application Priority Data

Oct. 12, 2005 (NL) ....................................  1030174

(51) Int. Cl.
```
F25D 23/00    (2006.01)
A61L 9/20     (2006.01)
F24F 3/16     (2006.01)
```

(52) U.S. Cl.  
CPC ................ *A61L 9/205* (2013.01); *F24F 3/166* (2013.01); *F24F 2003/1667* (2013.01)

(58) Field of Classification Search  
CPC .......... F25D 2317/04; F25D 2317/041; F25D 2317/0417; F25D 17/042; F25D 27/00  
USPC ........ 62/78, 264–265, 237, 186, 408; 96/224; 422/24, 121; 454/3–10, 22, 27, 72, 454/232, 234, 243, 248, 256, 322, 333; 236/49.3  
See application file for complete search history.

(56) References Cited

U.S. PATENT DOCUMENTS

| | | | |
|---|---|---|---|
| 3,699,747 A |   | 10/1972 | Kroll |
| 4,242,882 A | * | 1/1981 | Abraham ......................... 62/256 |
| 4,288,115 A | * | 9/1981 | Sullivan ......................... 285/363 |

(Continued)

FOREIGN PATENT DOCUMENTS

| | | |
|---|---|---|
| DE | 100 06 575 | 8/2001 |
| DE | 102 09 994 | 9/2003 |

(Continued)

*Primary Examiner* — Cheryl J Tyler  
*Assistant Examiner* — Orlando E Aviles Bosques  
(74) *Attorney, Agent, or Firm* — The Webb Law Firm

(57) ABSTRACT

An auxiliary device is tended and adapted to be accommodated in an air conduit forming part of an air conditioning device, to which air conduit first flow components, such as a fan, are connected for the purpose of bringing about a main airflow through the air conduit such that the whole main airflow flows through the auxiliary device. The auxiliary device has an arrangement of a number of air conditioning modules which in an active state of the relevant air conditioning module, each allow passage of a partial flow of the airflow and together allow passage of the whole main flow. Control components adjust each of the air conditioning modules between an active state, in which passage of the relevant partial flow is allowed, and a passive state in which a partial flow substantially amounts to zero or flows in opposite direction.

21 Claims, 20 Drawing Sheets

(56) References Cited

U.S. PATENT DOCUMENTS

| | | | |
|---|---|---|---|
| 4,352,349 A * | 10/1982 | Yoho | 126/299 R |
| 4,433,244 A * | 2/1984 | Hogan | 250/455.11 |
| 5,330,722 A | 7/1994 | Pick et al. | |
| 5,612,001 A | 3/1997 | Matschke | |
| 5,933,702 A * | 8/1999 | Goswami | 422/186.3 |
| 6,057,917 A * | 5/2000 | Petersen et al. | 356/213 |
| 6,221,314 B1 * | 4/2001 | Bigelow | 422/24 |
| 6,322,614 B1 | 11/2001 | Tillmans | |
| 6,497,753 B1 | 12/2002 | Gutmann | |
| 2002/0088945 A1 | 7/2002 | Matschke | |
| 2003/0021721 A1 * | 1/2003 | Hall | 422/4 |
| 2003/0131734 A1 | 7/2003 | Engel et al. | |
| 2003/0186643 A1 * | 10/2003 | Feuillard et al. | 454/157 |
| 2004/0047776 A1 | 3/2004 | Thomsen | |
| 2004/0166018 A1 * | 8/2004 | Clark et al. | 422/4 |
| 2005/0173352 A1 | 8/2005 | Burrows et al. | |
| 2007/0119699 A1 * | 5/2007 | Chambers et al. | 204/176 |

FOREIGN PATENT DOCUMENTS

| | | |
|---|---|---|
| EP | 0 550 336 | 12/1992 |
| EP | 0915713 B1 | 8/2001 |
| EP | 1 239 232 | 9/2002 |
| GB | 1382820 A | 2/1975 |
| GB | 2 377 660 | 1/2003 |
| NL | 7307984 | 6/1973 |
| WO | WO 92/20974 | 11/1992 |
| WO | WO 98/26810 | 6/1997 |
| WO | WO 02 078754 | 10/2002 |
| WO | WO 03/008069 | 1/2003 |
| WO | WO 03 045451 | 6/2003 |
| WO | WO 03/078571 | 9/2003 |
| WO | WO 2004/011041 | 2/2004 |
| WO | WO 2005/039659 | 5/2005 |

\* cited by examiner

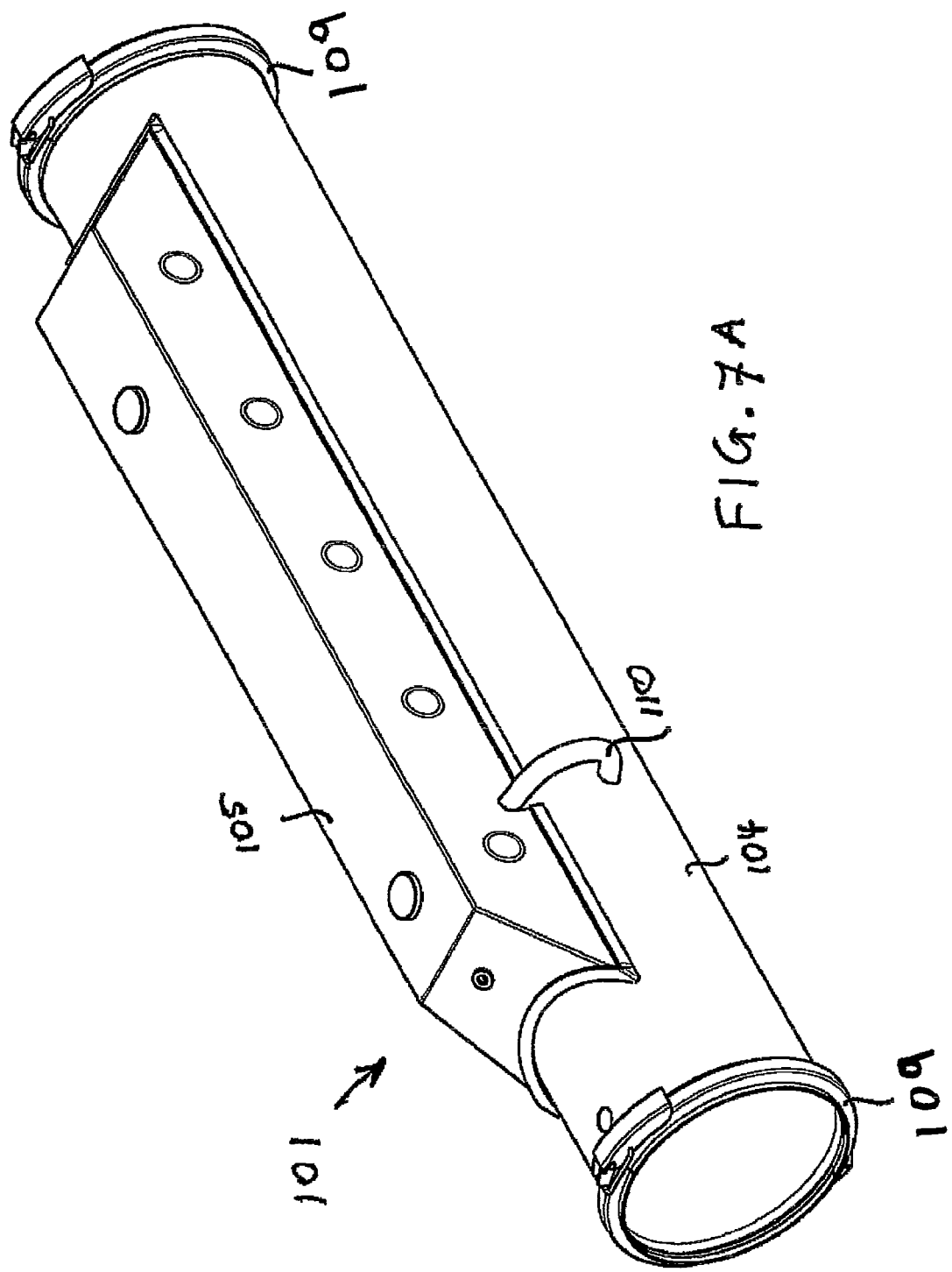

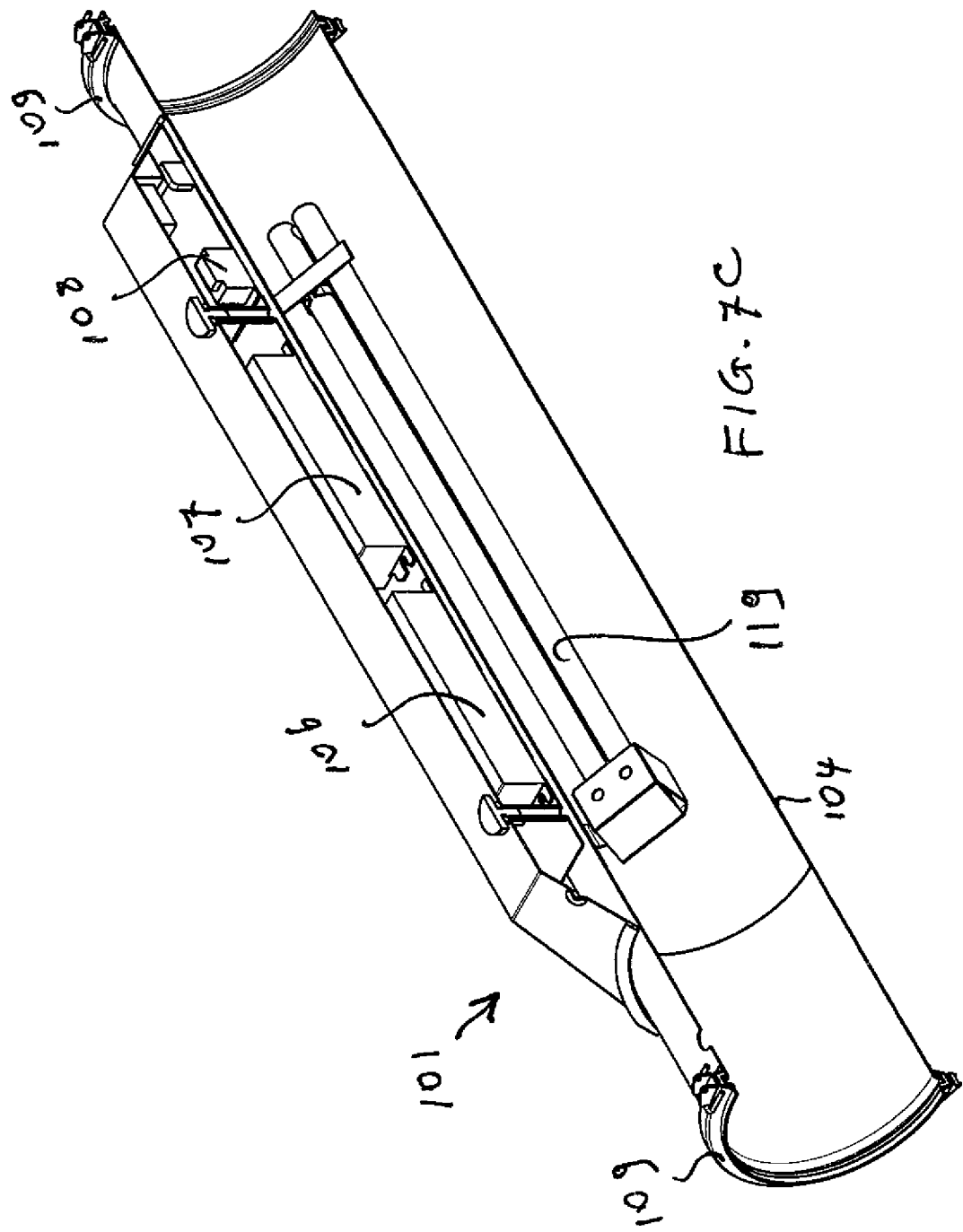

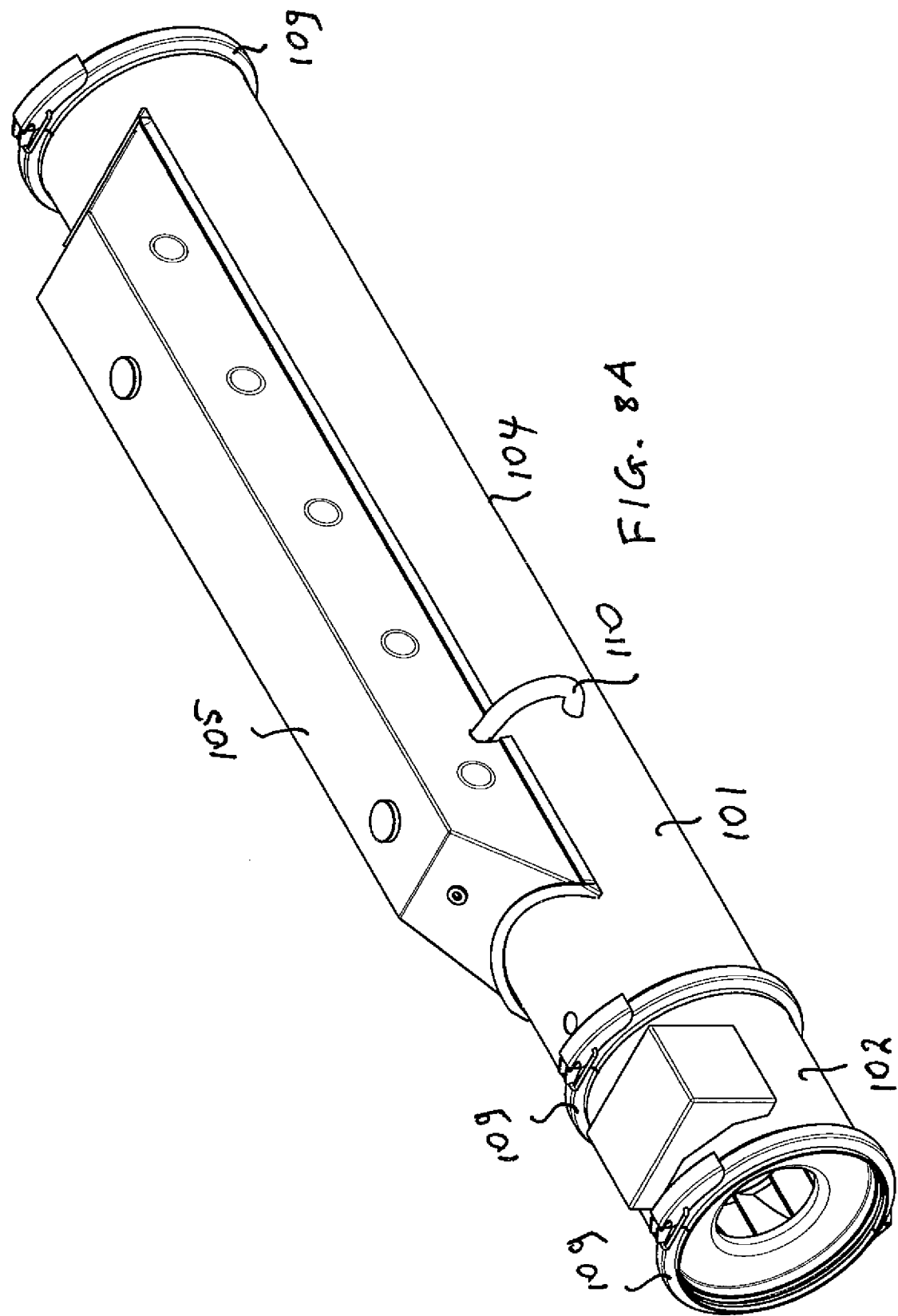

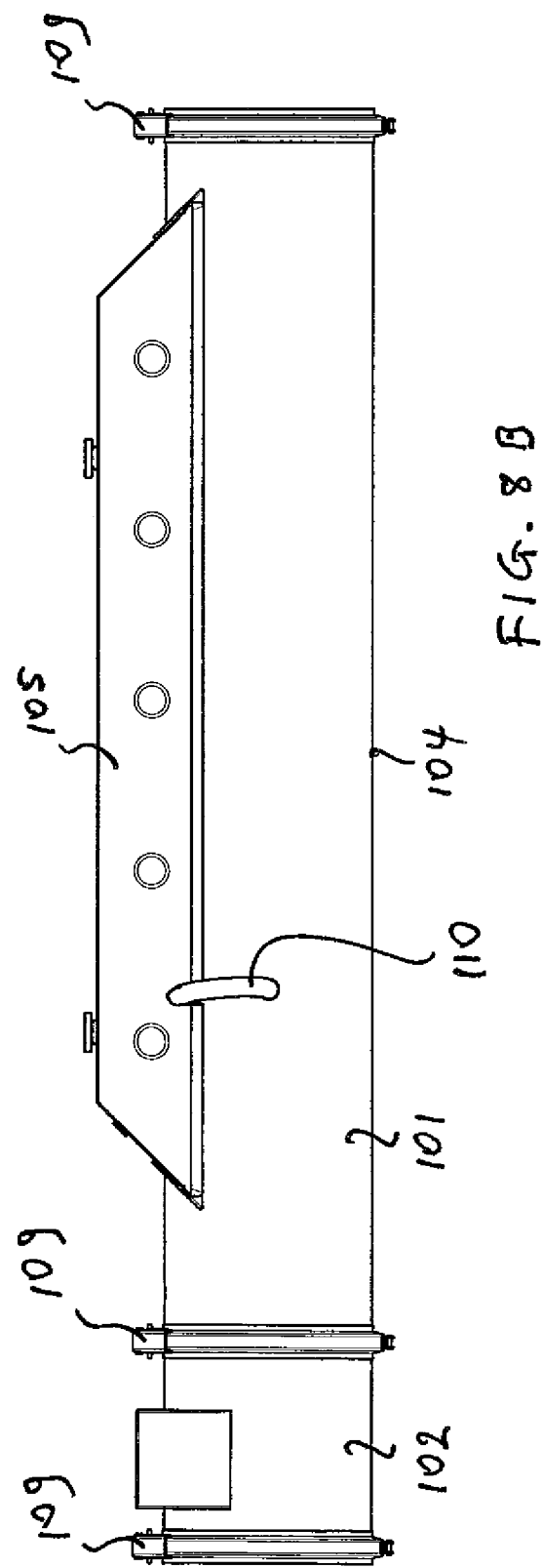

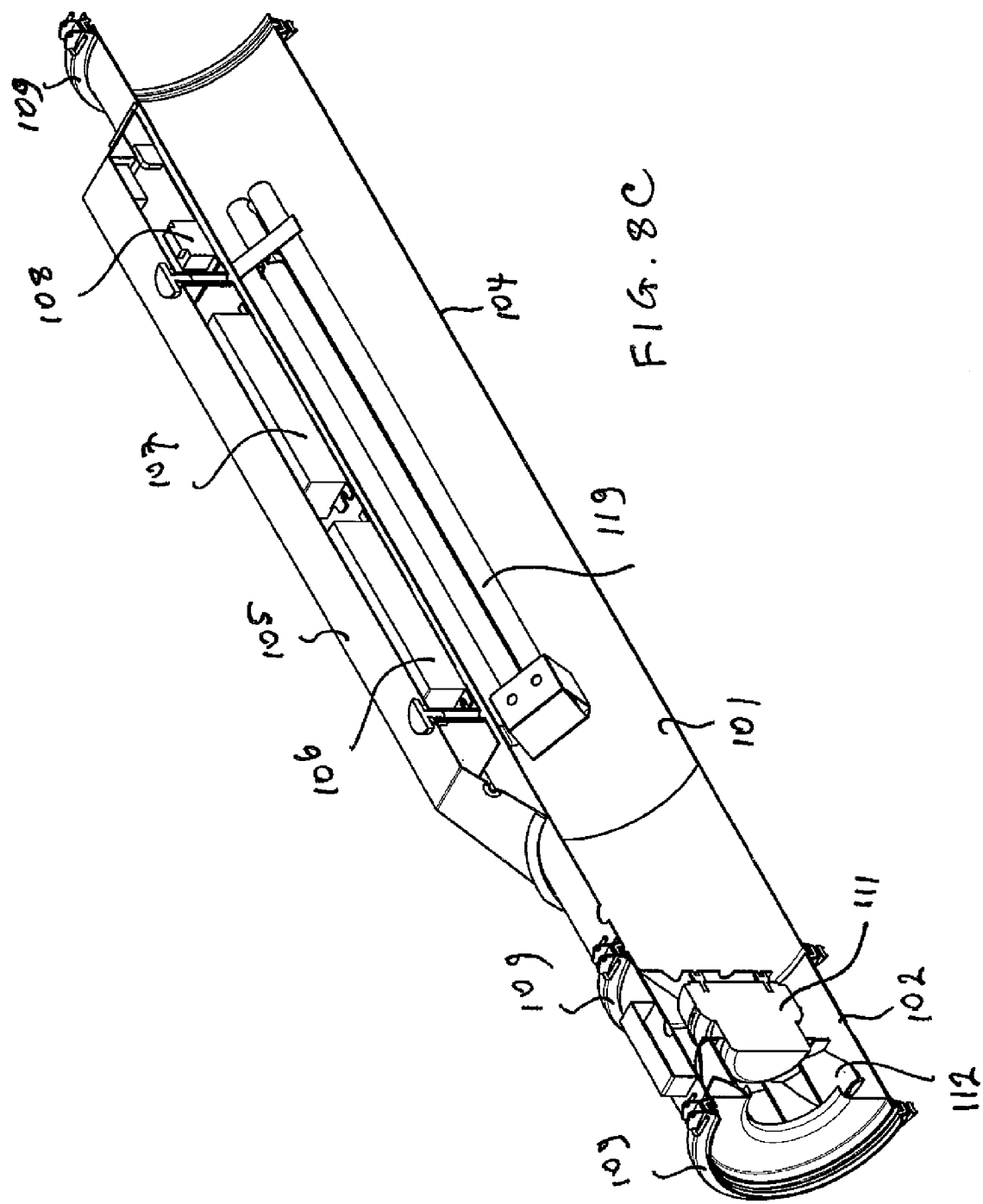

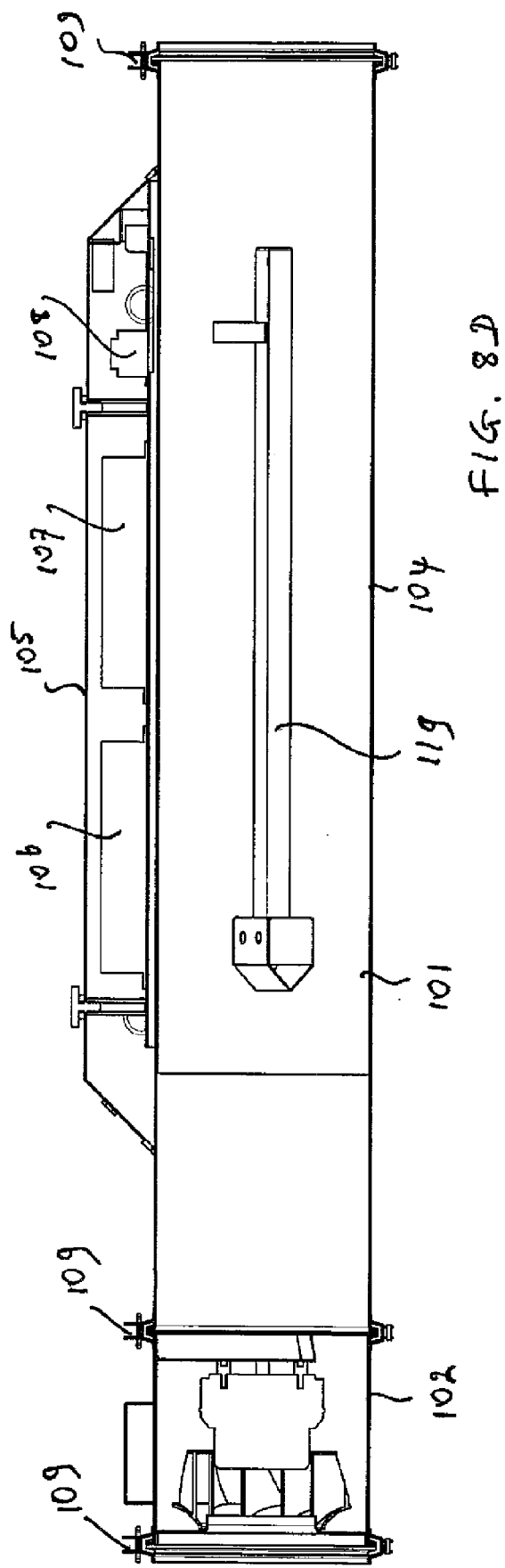

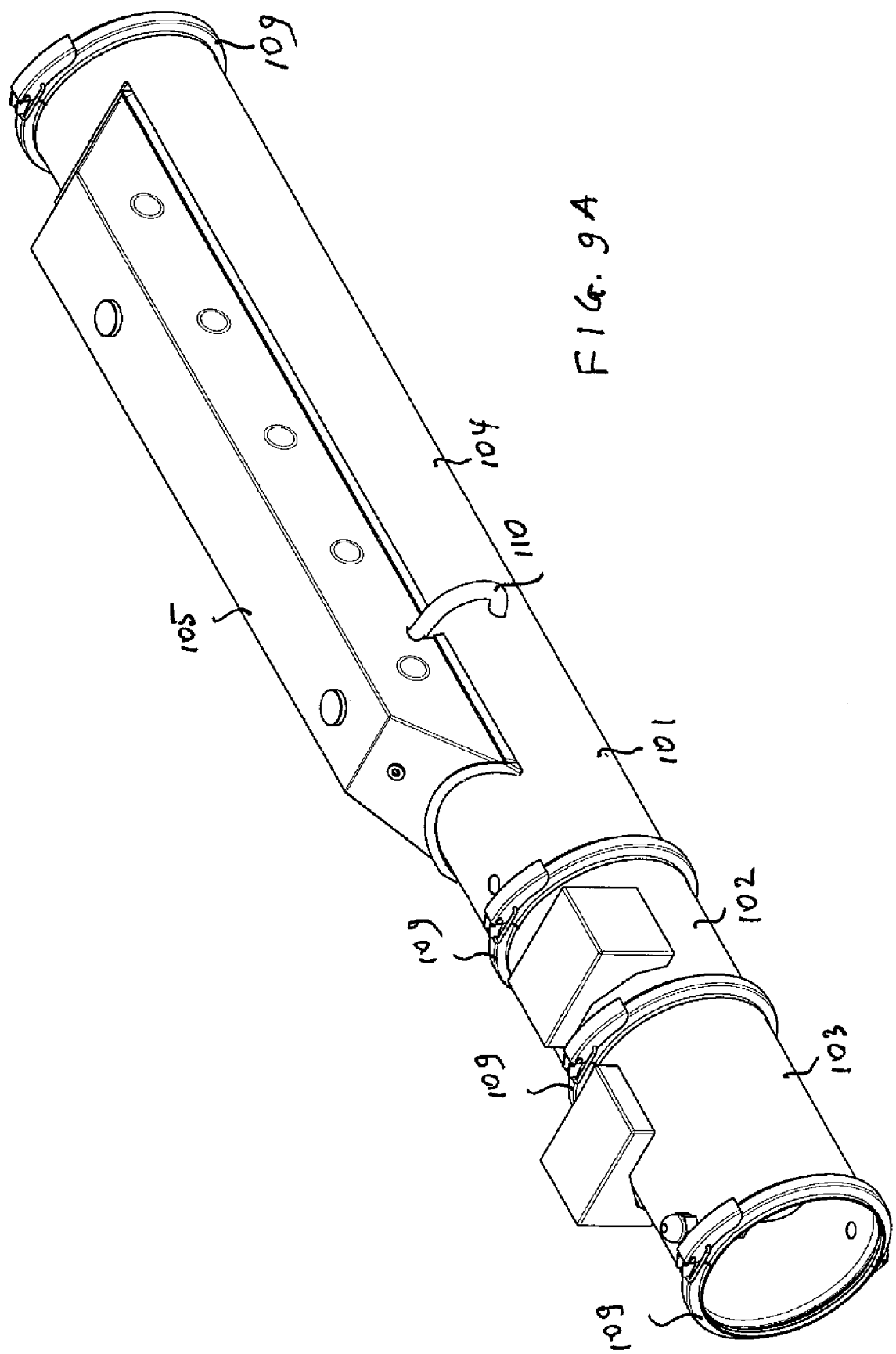

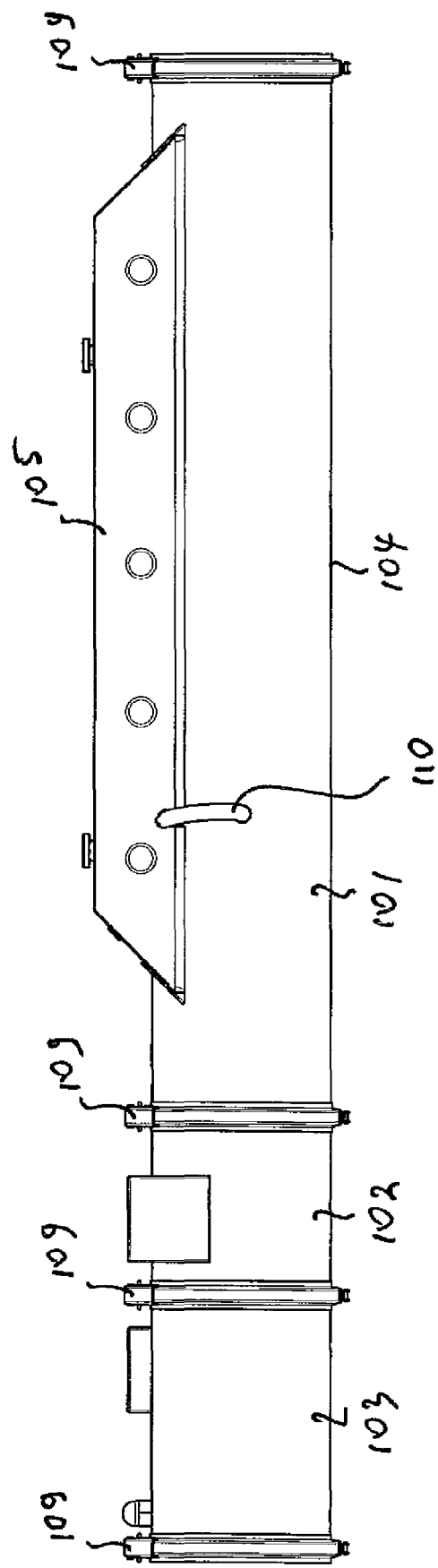

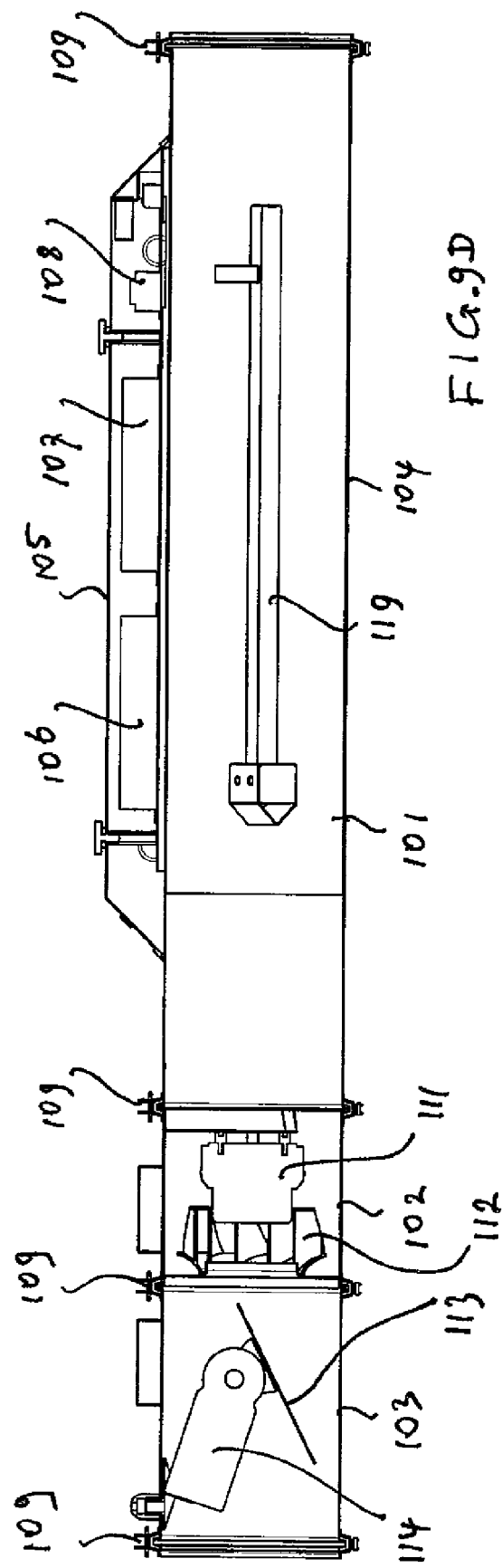

AUXILIARY DEVICE INTENDED FOR ADDING TO AN AIR CONDITIONING DEVICE

BACKGROUND OF THE INVENTION

Field of the Invention

The invention relates to an auxiliary device intended and adapted to be accommodated in an air conduit extending between a first air feed and a first air discharge and forming part of an air conditioning device, for instance an air freshening system, an air filtering system, an air cleaning system or the like, comprising a feed part and a discharge part, to which air conduit first flow means are connected for the purpose of bringing about a main airflow through the air conduit such that the whole main airflow flows through the auxiliary device.

Such an auxiliary device is for instance known in the form of a filtering device, a drying device, a humidifying device, a cooling device, a heating device or the like which is added in said manner to an air conditioning device.

SUMMARY OF THE INVENTION

The auxiliary device according to the invention comprises an arrangement of a number of air conditioning modules which, in an active state of the relevant air conditioning module, each allow passage of a partial flow of the airflow and together allow passage of the whole main flow; and control means for individually adjusting each of the air conditioning modules between an active state, in which passage of the relevant partial flow is allowed, and a passive state in which the partial flow substantially amounts to zero or flows in opposite direction.

The auxiliary device including the air conditioning modules have a modular structure. The device can hereby be readily adapted to conditions and to requirements varying over time. The number of installed or active air conditioning modules can for instance be chosen as required, either at the design stage or also after installation and during operation. The modules can thus be controlled individually by a central control unit. In the case of a module serving for heating or cooling the control can for instance hereby take place such that the flow rate, i.e. the amount of air passing through per unit of time, meets the set requirements, taking into account the set requirements in respect of the air discharge temperature or the difference between the air infeed temperature and the air discharge temperature. It will be apparent that this is only one example.

Particularly in the case where the air conditioning modules are identical the modular structure has the advantage that an air conditioning module which is malfunctioning or must otherwise be serviced can be removed and replaced by another module with relatively simple operations. The technical measures necessary for this purpose are very limited due to the modular structure.

The invention can in an abstract sense be described as follows.

Physical processes are in general instable around an optimum. In view thereof a designer calculates on basis of a certain safety margin in order not to go outside the optimum process window.

The invention solves this problem by initially determining an optimal process and subsequently simply multiplying a number of these processes in the form of implementation in modules until the desired capacity is achieved.

In other words: the described modularity is the adding or removing, respectively, of equal optimal process modules in order to realize the total process capacity.

Relative to the prior art this is an improvement, since in the prior art only another operating point in an existing process window is adjusted in order to realize the new capacity.

Since a process window in most cases exhibits only one single optimum, another operating point automatically implies a deterioration of the process.

According to the invention every active process is always maintained within its optimum operating range.

It is further of great importance that the manufacturer of auxiliary devices of the type according to the invention need only stock and be able to supply a limited number of different types of air conditioning module. It is thus also possible to anticipate the wishes of users in very rapid and flexible manner. It is possible to take into account varying requirements set for the capacity of an air conditioning device by modifying the housing to the set requirements, particularly in respect of the effective passage area, and to select the number of modules desired in respect of the set requirements.

The auxiliary device can be designed to fulfill a wide range of varying functions, such as filtering of air, cleaning of air, drying or humidifying of air, cooling or heating of air, disinfecting and sterilizing of air and so forth.

In yet another embodiment the auxiliary device has the special feature that each air conditioning module comprises: a second housing with a third air feed and a third air discharge; and a UV treatment chamber which is received in this housing and through which the whole partial flow flows, in which UV treatment chamber a UV radiation source is accommodated for the purpose of exposing the partial flow to UV radiation in order to kill micro-organisms present in this partial flow.

If the air speed in the UV treatment chamber changes, the time for which micro-organisms are exposed to UV radiation also changes. A stable degree of sterilization requires in this respect a substantially constant air speed. This air speed also influences the sterilization on the basis of another physical mechanism which comes into play in the UV treatment chamber. The air flowing along the UV source also serves to cool this source. It should be understood that when the air speed changes the temperature of the UV source also changes. The intensity of the UV radiation emitted by the source is found to depend on the temperature. The UV intensity is maximal at a determined temperature; at a lower temperature the intensity decreases and at a higher temperature the intensity likewise decreases. It has been demonstrated that, for a UVGI lamp, an air speed of about 1.5 m/s (in the case of the use of more lamps this air speed may be higher) at a temperature of the admitted air corresponding to room temperature produces the highest intensity. Assuming that this infeed temperature remains unchanged, a constant air speed is therefore important.

A constant air speed is also of very great importance for the efficiencies of other thermodynamic processes like cooling, heat exchanging, humidifying, dehumidifying, etc. As already mentioned, by means of (velocity) stabilization of these processes by means of the present invention a substantially higher efficiency and correspondingly lower energy consumption can be achieved. Designers are in a position to calculate on basis of much smaller safety factors (on the edge design).

Light arrays and grids have a fixed cross-section in terms of height times width. When in the case of a fixed cross-section the flow rate of the supplied air changes, the speed through the auxiliary device then also changes in direct proportion thereto. There is a twofold effect on the degree of sterilization. As described above, it is hereby not possible to avoid that the micro-organisms to be exposed to UV radiation receive less than the desired radiation dosage of UV radiation. The UV source becomes colder or warmer and hereby operates in a range which varies from its optimal operating range, i.e. the operating range in which the emitted radiation intensity is maximal.

As stated, light arrays and grids have an unchanging, fixed cross-section. It is thereby not possible to control or regulate the speed of the airflow. The present invention is based on a modular construction, wherein the individual air conditioning modules can be opened or closed and adjusted. The passage area of the cross-section can thus be enlarged or reduced in size in steps, in modular manner, by respectively activating and deactivating the individual air conditioning modules. The flow speed can be regulated by this modular, variable cross-section according to the teaching of the invention. With reference to the above discussion relating to the radiation output of UVGI lamps, it can hereby be established that the residence time, the degree of sterilization realized, the cooling of the lamp and the radiation output are controllable, this in contrast to a known device of fixed cross-section. By switching off the lamps in (temporarily) unused air conditioning modules the lifespan of the lamps is increased and unnecessary energy consumption prevented.

The passage in the overall available throughflow area which is stepwise adjustable on a modular basis provides for an excellent process control at airflow rates which vary between wide limits.

The modular adjustability also has a number of additional advantages. The control software of the auxiliary device can thus be designed such that the effective throughflow area of the available cross-sectional area is also adjusted in the case of changes in the temperature of the inflowing air and/or the relative humidity thereof. Using such software the critical sterilization process can always proceed on a continuous basis under optimum conditions. With the use of this software fluctuations in the flow rate of the supplied air, the temperature of the supplied air and the relative humidity of this air have no marked effect on the degree of sterilization, which is after all indicative of the quality of the device according to the invention with a UV treatment chamber. The effective lifespan of the lamps is increased by switching off unused lamps, since switching off lamps can take place under software control such that different lamps are switched off each time. In addition to a long lifespan of the lamps, a high energy efficiency is also realized here.

In an important embodiment the auxiliary device according to the invention has the special feature that a valve controllable between an open and a closed position by the control means is accommodated in each air conditioning module. The valve can be of any suitable type. Operation can take place in electrical, hydraulic, mechanical or pneumatic manner. In the case where the control means comprise a central processor which controls the diverse modules of the program control and under control by means of operating means to be operated by a user, the valves must all be electrically controllable. In such an embodiment hand control is for instance not deemed suitable as the first option.

In respect of said valves the modular structure can have the further advantage that for instance the flow rate through each active module always has a predetermined value, and that the main airflow, i.e. the sum of the partial airflows through the active modules, is therefore directly proportional to the number of active modules.

The auxiliary device can also have the special feature that second flow means controlled by the control means are accommodated in each air conditioning module for the purpose of setting the partial flow to a desired value, being either positive, zero or negative.

These second flow means can for instance be embodied as a fan. Connection of modules to external sources for air under a certain overpressure can also be applied.

In the case of larger clusters a sudden increase of the air supply to the modules may result in an increase of the airflow passing the inner modules and a decrease of the airflow through the outer modules. A valve will in this case choke the modules through which too much air flows, so that the airflow is decreased, and the other modules receiving too little air now receive an increased amount of air.

The killing of micro-organisms in an airflow by means of irradiation with ultraviolet radiation is per se known, inter alia from applicant's international patent application WO-A-2005/039659, and further from US-A-2004/0047776, WO-A-02/078754, GB-A-1 382 820, EP-A-1 239 232, EP-A-0 550 366, DE-A-102 09 994, NL-A-73 07984, EP-A-0 915 713, WO-A-03/078571 and GB-A-2 377 660.

The air in which we live contains bacteria, viruses and other micro-organisms which, under determined conditions, can cause disease in humans or animals. In a hospital environment this risk of infection is considerable since here a combination is to be found of a relatively large number of pathogenic micro-organisms in the air, the possible presence of patients with an infectious disease and the presence of weakened patients who are extra-prone to infection. In the relatively closed buildings in which people nowadays work pathogenic organisms can also spread easily via air conditioning systems. In addition, the disinfecting of air is important under non-permanent conditions which can occur after for instance the outbreak of an infectious disease caused by viruses or after the use of biological weapons. In these situations it will be necessary to provide temporary command centres, emergency hospitals and other important accommodation areas with disinfected air, if necessary from displaceable air conditioning systems.

The sterilization of a forced airflow using ultraviolet radiation of short wavelength UV(C), i.e. radiation with a wavelength in the range 100-280 nm, is per se known. Usually used for this purpose are appliances which are freestanding or mounted on a wall or a ceiling and which causes the air in a space to circulate, and the protective effect of which is limited to this space. Such "germicidal air purifiers" intended for one space are described in U.S. Pat. No. 5,330,722 and U.S. Pat. No. 5,612,001. Developments of these freestanding appliances have been focused on a greater effectiveness in respect of killing micro-organisms while producing an air output which is as high as possible. Considerably improved performance has been achieved by applying filters with a low air resistance upstream of the UV treatment chamber, choosing inner walls with good reflection in the UV treatment chamber and creating a turbulent airflow along the UV lamps. Reference is made in this respect to WO-A-2005/039659 in the name of the present applicant.

Air conditioning devices circulate, freshen, dry, moisten, heat and/or cool the air in buildings. The air is carried from and to the different spaces in the building by a network of air ducts and air distribution systems, wherein micro-organisms can move effectively through the building and become easily lodged in the air ducts.

A frequently applied technique for eliminating micro-organisms in air conditioning systems is the incorporation of different types of air filter. Dust particles on which micro-organisms are often to be found are trapped by these filters, but smaller micro-organisms pass through the filters. The killing of the smaller micro-organisms using UV(C) radiation has also found application in air conditioning systems. Initially the UV lamps were simply placed perpendicularly of the flow direction in the air duct, whereby breakage could easily occur at the position of the lamp fitting as a result of bending.

The effectiveness of the lamps can be improved by placing a group of lamps in longitudinal direction of the air duct. According to WO-A-92/20974 the lamps placed in lengthwise direction of the duct are enclosed by helical baffles which carry the air in a helical flow around the lamps and thereby increase the path that is covered and the time of exposure. A perforated and bent plate is also placed downstream of the UV lamps with the purpose of achieving a more uniform distribution of the airflow over the cross-section of the duct and thereby limiting zones of less effective radiation, or even dead spots. In order to improve the effectiveness of the radiation a UV treatment chamber is described in US-A-2002/0088945 in the form of an ellipsoid which fits tightly into the air duct. The UV lamp takes the form of a helix, the axis of which coincides with the axis of the ellipsoid.

Although within a twenty-four hour timespan there can occur considerable periods without or with little activity in an air conditioning system, the UV lamps remain switched-on continuously in most installations. If the lamps are switched on together with for instance a fan forming part of the air heating, frequent switching on and off of the lamps can then have a greater adverse effect on the lifespan of the lamps than leaving them on continuously. In WO-A-03/045451 an effective increase in the lifespan of the UV lamps is claimed in that the lamps are switched off only after a longer period (40 minutes) of inactivity of the air conditioning system.

In the design of air conditioning systems for buildings having spaces therein in which patients can be isolated the difference in pressure between these spaces and the environment is of great importance. A distinction must be made between "overpressure" and "underpressure" spaces. Overpressure protects a patient in for instance operating theatres from infection from the environment. Underpressure protects the environment from infection with for instance a virus which can be spread by a patient.

Under non-permanent conditions the ability to isolate and disinfect patients is often also important, for instance after the outbreak of an infectious disease caused by viruses or after the use of biological weapons. In these situations it will be necessary to provide temporary command centres, emergency hospitals and other important accommodation areas with disinfected air and, if necessary, to isolate them. US-A-2004/047776 and WO-A-2004/011041 describe displaceable "air decontamination devices" which can be utilized in the case of calamities of the stated type.

Freestanding appliances for treating the air in one space with UV(C) radiation are, due to developments such as described in WO-A-2005/039659 in the name of the present applicant, much more effective than the UV© systems for killing micro-organisms incorporated into fixed air conditioning systems. The cause of this lies in the generally large dimensions of the fixed systems and the problem of good distribution of the airflows over the cross-section of the air ducts in these systems. In addition to the drawback of limited effectiveness, UV lamps in existing air conditioning systems still have a long duty cycle, also in periods when the requested activity of the system may be low.

In determined embodiments the present invention obviates the stated drawbacks of the prior art and adds a number of control means for the flow along the UV lamps, whereby a wider application of UV(C) systems for killing micro-organisms will be obtained. The applicability will be increased further by the flexible utilization in overpressure and underpressure situations during isolation of patients in existing and temporary spaces and in the case of calamities.

Specific advantages are realized with an embodiment in which the second flow means comprise a fan which is of the type with angularly equidistant blades which are present on a rotor driven by a motor and the inner edges of which lie substantially on an imaginary cylinder and the outer edges of which lie at least more or less on an imaginary truncated cone, these outer edges forming together with an at least more or less cylindrical envelope a free space widening in the direction of the flow. The use of such a fan gives the auxiliary device a high measure of flexibility since the flow rate produced by the fan is adjustable from the value zero to relatively high values under the influence of a control unit, the noise production is very low, certainly in relation to the performance, and the difference in pressure produced by the fan, while being slightly lower than that of a purely axial fan, nevertheless still has very acceptable values. Such a fan is commercially available per se from the German firm EBM-Pabst, with among others the model specification R3G133-AF07-14.

In addition to the above stated general advantages of the modular structure, the device according to the invention has the following advantages in respect of treatment of through-flow air with UV radiation.

The auxiliary device is able to disinfect airflows in an existing, fixedly disposed or mobile air conditioning device, whereby the micro-organisms present in the airflows can effectively be eliminated.

Despite the great variety of dimensions of air ducts in existing air conditioning devices, the auxiliary device according to the invention can be built into new and existing systems with a relatively small investment.

Installation and maintenance can take place easily and at relatively low cost compared to existing systems. Specifically by eliminating the need of using service hatches before or after installation the maintenance is substantially simplified. A service operator has direct access to the modules.

As a consequence of the modular character and the possibility of optimizing the diverse parameters in relation to each other, the auxiliary device according to the invention can have a high energy efficiency.

The auxiliary device can comprise a control means for switching the UV lamps on and off. Other than in existing devices, the effective lifespan of the lamps can hereby be prolonged considerably. It will be apparent that this provides the advantage of the lamps having to be replaced less frequently. This means a cost-saving and a longer time between standstill periods of the relevant module for the purpose of replacing the lamps.

A regulation of the airflow along the lamps can take place in simple manner such that the lamps are always in operation at an optimal temperature. This temperature determines the intensity of the UV radiation generated by a lamp and the lifespan of the lamp. Furthermore the modularity offers the possibility to first switch the lamps on so that they reach the correct temperature before the valve is opened. Herewith it is effectively avoided that the first air is not sterilized in an optimum manner.

The air speed can further be adjusted, for instance by modified control of a fan, or the adding of the correct number momentarily closed modules, such that the more moist the flow-by air is, the longer the time the air remains in the UV treatment chamber. Such a regulation can be important in order to ensure that, despite the shielding effect against UV radiation of water around micro-organisms, these micro-organisms can nevertheless be effectively eliminated.

The device can further be applied in simple manner under the said overpressure and underpressure conditions. This aspect may for instance be important in the case of spaces where patients must be temporarily isolated.

The auxiliary device according to the invention is highly suitable for building into both fixed and displaceable air conditioning devices.

A UV treatment auxiliary device comprises at least one UV lamp which is accommodated in a UV treatment chamber. If desired, although not essential, each air conditioning module can be provided with said second flow means, such as a fan. An electronically controllable valve can be applied to close a module. After closing off this valve and/or energizing of off the fan such that the airflow through a module amounts to zero or, in some conditions, an airflow flows in opposite direction, the relevant UV source, consisting of at least one UV lamp and the optionally present fan, of the relevant module can be switched off.

In periods of low activity of the air conditioning device or in the case of a low momentary load of micro-organisms, the capacity of the device can be adjusted to these conditions by guiding the airflow along only a limited number of active, so switched on, modules.

The average lifespan of the UV lamps in the auxiliary device is prolonged by activating the air conditioning modules in a sequence and keeping them activated for a determined time using a processor such that the cumulative duty cycle of all UV lamps is always more or less the same.

In the case where a lamp fails the relevant module is effectively deactivated by closing the valve that is present or by causing the associated fan to rotate in reverse direction, and the other modules can continue to function normally without the occurrence of a leakage over the total airflow, which effectively is the case with designs according to the prior art.

In a determined embodiment the auxiliary device according to the invention does not influence the flow rate in the air conduit. The fan in the module compensates the pressure loss resulting from the air resistance of the module itself by means of a "pressure difference control". This microprocessor-controlled system provides for a small increase in pressure (1-5 mbar) over the modules so that no leakage of non-treated air through the closed valves can occur. The air can even flow in opposite direction at a low flow rate.

When applied for the purpose of "overpressure" spaces, the device is placed as closely as possible to the inlet point to the "overpressure" space in question.

When applied for the purpose of "underpressure" spaces, the device is placed immediately downstream of the outlet point of the space in question, and it is recommended, for instance for application in medical areas, to also place an auxiliary device according to the invention in the inlet duct in order to protect the isolated and weakened patient from the pathogenic bacteria normally present in the air.

Use of the auxiliary device in mobile air conditioning devices is possible because the auxiliary device is integrated into a section of a conduit system which can also be added in simple manner to displaceable air conditioning devices.

An embodiment of the auxiliary device of the embodiment with a UV treatment module preferably comprises adjusting means for adjusting the UV radiation source such that the intensity of the UV radiation emitted by this source lies in the operating range of the source where this intensity differs by less than 10%, preferably less than 5%, from the maximum intensity. The operation of the auxiliary device can hereby be optimized.

An important embodiment of this latter principle has the special feature that the adjusting means are adapted to adjust the speed of the air flowing along the source and thus cooling the lamp.

In a specific embodiment this latter auxiliary device has the special feature that the adjusting means are controlled by temperature measuring means which measure the difference between the outlet temperature and the inlet temperature of the UV treatment chamber. Thus the energy transfer between the lamp and the air is determined. When this changes, this means in accord with known laws of thermodynamics, that mainly the air velocity has changed (irrespective of changes in the in feed temperature). Herewith also the airflow or air velocity through each module may be derived on an individual basis. This information is then used by the control system in order to assess, whether too many or too few modules are in their active states.

Alternatively, the auxiliary device can have the feature that the adjusting means are controlled by intensity measuring means which measure the intensity of the UV radiation emitted by the UV radiation source.

According to another aspect of the invention, the auxiliary device has the special feature that at least a part of the surfaces irradiated by UV radiation is provided with a PTO (photocatalytic oxidation) coating, consisting for instance of $TiO_2$ (titanium dioxide). Unpleasant odours and smoke can hereby be effectively eliminated. A PTO material has the effect when irradiated by ultraviolet radiation of converting organic materials substantially wholly into $CO_2$ and $H_2O$.

A practical variant of the latter embodiment has the special feature that the device comprises a fan, and at least the surfaces of the fan irradiated by UV radiation, including the surfaces of the blades of the fan, are provided with a PTO coating.

According to an important further aspect of the invention, the auxiliary device also comprises at least one separate fan module and at least one separate valve module, wherein each air conditioning module, each fan module and each valve module can be sealingly coupled to each other in pairs in any desired arrangement, wherein all modules comprise substantially the same flanges, and flanges placed against each other are coupled releasably to each other by means of a divisible and closable ring, which in close position extends over both flanges and holds these flanges pressed against each other, this is such that the modules can be mutually coupled in modular manner in all desired numbers and in any desired arrangement. A high degree of modularity is realized with such an embodiment, whereby and in principal random number of modules can be coupled to each other in any desired configuration wholly in accordance with the wish of a user. An important embodiment has in this respect the feature that a valve module is placed at both the inlet side and the outlet side of an air conditioning module such that after closure of the valves of the two valve modules the air conditioning module can be removed without the need of switching off the other modules or the entire air supply system (safe change).

In a specific embodiment the auxiliary device has the special feature that the inner wall of the UV treatment chamber is provided with a reflective coating which is situated in the region of the UV source and extends further upstream and downstream over a distance at least equal to 40% of the length of the UV source in the lengthwise direction of the UV treatment chamber. This embodiment achieves a substantial increase in the efficiency of the UV radiation in the UV treatment chamber. The number of micro-organisms killed by the UV radiation while passing through the UV treatment chamber hereby increases.

This latter embodiment preferably has a special feature that the coating is diffusely reflective.

The invention also relates to an air conditioning device, for instance an air freshening system, an air filtering system, an air cleaning system or the like, comprising: and the auxiliary device of the above specified types.

This is an appropriate moment for a short discussion of the content of several references which, when examined superficially, appear to have an affinity with the invention. This is deceptive however, as the short analysis below will demonstrate.

US-A-2003/0131734 relates to an air cleaner which is embodied as a UV source and comprises on its outside a number of UV lamps with reflectors added thereto. FIG. 1 of this American specification shows that on the inlet side (in the direction of the airflow) there is placed a convex deflection cover described as parabolic which must ensure that the air flowing in lengthwise direction along the air cleaner flows along the whole length past the UV lamps.

FIG. 4 for instance shows the manner in which the UV sources can be placed in an air conduit.

It is important to note that this document does not relate to an "auxiliary device" as stated in the present patent application, i.e. a specific functional unit which must be added to an existing air conduit. The American specification shows and describes only a number of UV sources which, to all appearances, must all operate simultaneously and together provide a UV radiation intensity such that many organisms responsible for "sick building syndrome" are eliminated.

It is of further importance to note that this American specification does not mention air conditioning modules in the sense intended according to the invention. It is after all a central according to the invention that the modules each guide a partial flow of the total airflow. Since there is no mention of any separation in the airflow in the American specification, let alone of effective partial flows, the structure according to this document does not fulfil this definition according to the present invention.

U.S. Pat. No. 6,497,753 relates to an electrostatic air cleaner. This cleaner comprises a housing with a feed and a discharge, fan means and a number of electrostatic filter units placed parallel in the airflow.

Were although the American specification is not wholly clear on this, it appears probable that the individual filter tubes are defined by the physical mechanism of the electrostatic filters. The inventor of the apparatus according to this American specification evidently did not opt for a modular construction with the specific advantages such as are sought after with the present invention, and as they are documented in the above.

US-A-2005/0173 352 relates generally to an air cleaning device. Use is made here of a filter, a fan and a UV treatment chamber. Such devices are generally known and discussed comprehensively in the foregoing. The present invention does not however relate to such a device, the essential modularity according to the present invention is after all wholly lacking in this specification.

The invention will now be elucidated on the basis of the accompanying drawings of several random exemplary embodiments.

BRIEF DESCRIPTION OF THE DRAWINGS

FIG. 7A is a perspective view of an air conditioning module which can be coupled in modular manner;

FIG. 7C is a cut-away perspective view of the air conditioning module;

FIG. 8A is a view corresponding with FIG. 7A of the air conditioning module which is coupled in modular manner to a fan module;

FIG. 8B shows a view corresponding with FIG. 7B of the modular unit of FIG. 8A;

FIG. 8C is a view corresponding with FIG. 7C of the modular unit of FIG. 8A;

FIG. 8D is a view corresponding with FIG. 7D of the modular unit of FIG. 8A;

FIG. 9A is a view corresponding with FIG. 7A of a modular unit assembled from an air conditioning module, a fan module and a valve module;

FIG. 9B is a view corresponding with FIG. 7B of the modular unit of FIG. 9A;

DETAILED DESCRIPTION OF THE INVENTION

Figure 1:
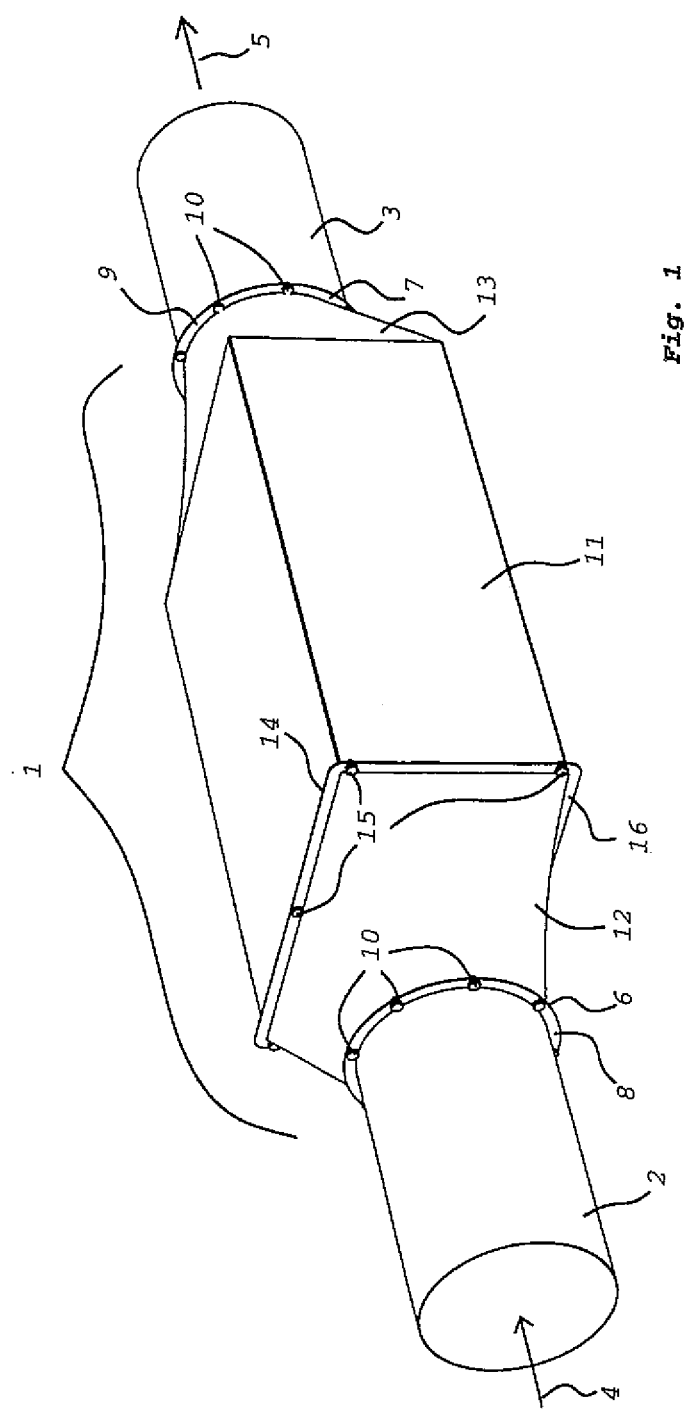
FIG. 1 is a perspective view of an auxiliary device which is received in an air conduit forming part of an air conditioning device.

FIG. 1 shows an auxiliary device 1 which is arranged in the manner of a conduit part in an air conduit comprising a feed apart 2 and a discharge part 3, which air conduit forms part of an air conditioning device (not drawn). Air flows through feed part 2, auxiliary device 1 and discharge part 3 of the air conduit. The direction thereof is indicated with arrows 4, 5. Auxiliary device 1 comprises round end flanges 6, 7, using which the auxiliary device 1 is connected to tubular parts 2 and 3, which are provided for this purpose with respective corresponding flanges 8, 9. Flanges 6, 8 and 7, 9 respectively are releasably coupled to each other by means of bolts and nuts 10. In the above described way the auxiliary device 1 can form part, in the manner of a tube part, of the air conduit comprising conduit parts 2, 3. This is an important aspect of the invention. Auxiliary device 1 can after all be added to an existing air conditioning device in this way.

Auxiliary device 1 comprises a housing 11, for instance of plate material or plastic, and has a generally rectangular cross-section. An inlet hopper 12 and an outlet hopper 13 connect to the housing. These hoppers 12, 13 adapt the cross-sectional forms of conduit parts 2 and 3 to the cross-sectional form of the block-like housing 11.

Situated on the inlet side of housing 11 is a flanged edge 14 connected sealingly by means of bolts and nuts 15 to a flanged edge 16 forming part of inlet hopper 12.

Figure 2B:
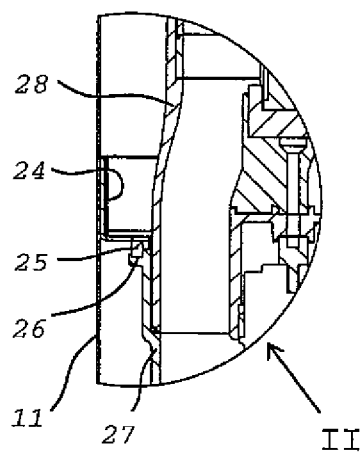
FIG. 2B shows on enlarged scale the detail II of FIG. 2A.
Figure 2A:
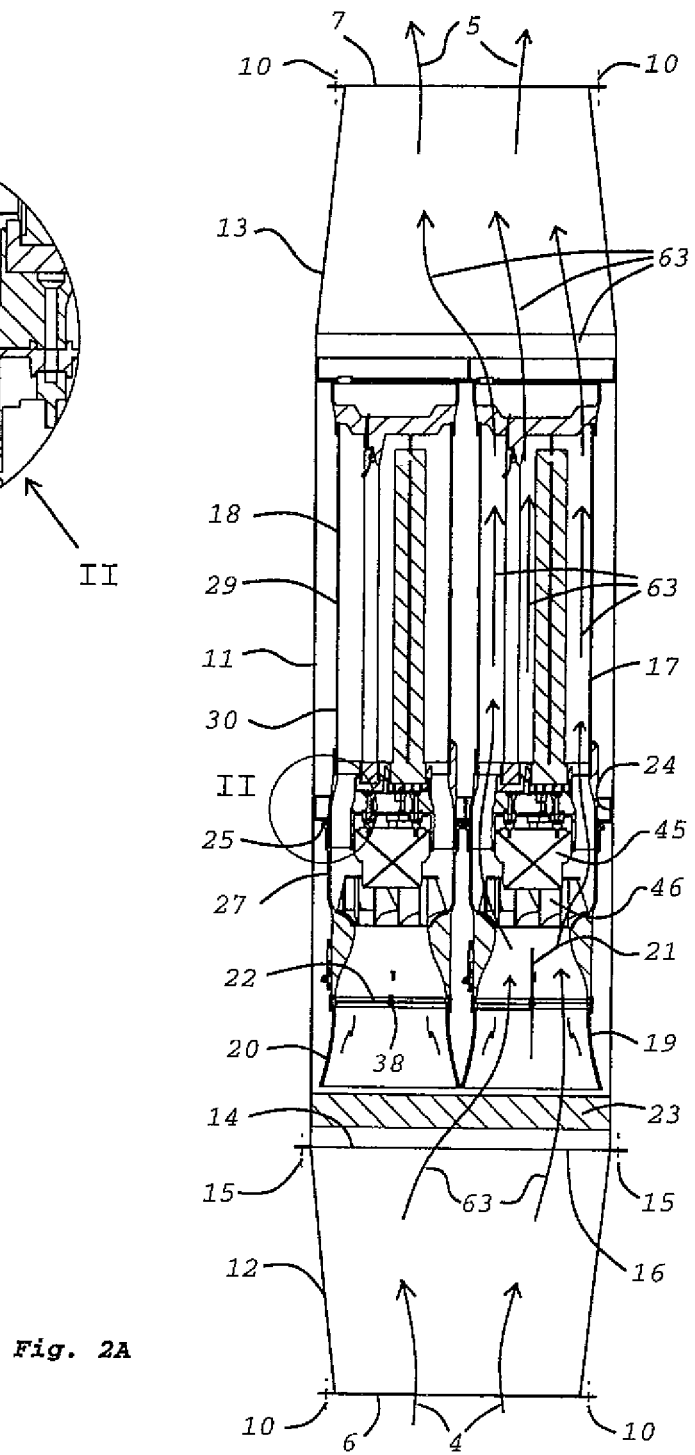
FIG. 2A shows a longitudinal section through the auxiliary device of FIG. 1.

FIG. 2A shows a longitudinal section corresponding to the relatively narrow side of housing 11. FIG. 2A shows that two UV air conditioning modules 17, 18 are present at the position of this longitudinal section. Although not shown in the drawing, it will be apparent from FIG. 2A and the proportions of housing 11 according to FIG. 1 that these UV air conditioning modules are disposed in a 2×3 matrix pattern.

The air conditioning modules are identical, and thus mutually interchangeable. FIG. 5A shows a longitudinal section corresponding with FIG. 2A of an air conditioning module, designated in this case with the reference numeral 17.

FIG. 2A is of particular importance because this figure makes clear the manner in which the air conditioning modules 17, 18 and the other four modules are arranged in housing 11.

Anticipating this discussion, attention is now already drawn to the inlet zones 19, 20 of module 17 in which are accommodated valves 21, 22 which can be displaced between an opened position and a closed position by means to be described below. In the situation of FIG. 2A valve 21 is open while valve 22 is closed. This is the reason why, as indicated with arrows 63, the airflow 4, 5 flows only through module 17 and not through module 18.

Attention is also drawn to the presence of a filtering unit 23 which cleans the throughflowing air of particles which are larger than the size of the filter pores. A relatively coarse dust filter can be applied to trap dust. For smaller particles and determined micro-organisms use can be made of a dust filter in combination with a HEPA filter. Reference is once again made in this respect to the international patent application WO-A-2005/039659 in the name of the present applicant, in which such filtering means are described, and to the literature cited in this specification. Housings 30 of modules 17, 18 and the other four modules must co-act substantially sealingly with the inner side of housing 11. For this purpose this housing 11 comprises on its inner side a sealing profile 24 which extends over the whole outer periphery of housings 30 and which co-acts sealingly via an elastically compressible sealing ring 25 with a peripherally extending ring seat 26 forming part of the lower part 27 of module housing 30, the central part of which is designated 28 and the upper part 29.

FIG. 2A further shows that outlet hopper 13 is formed integrally with block-like housing 11, as also shown clearly in FIG. 1.

Inlet hopper 12 is releasable by means of the bolts and nuts, whereby after removal of filter unit 23 the interior of housing 11 is accessible for the purpose of sliding out a module for maintenance purposes and replacing thereof or for the purpose of replacement by another identical module. As stated, the seal 24, 25, 26 extending peripherally around each module ensures that the pressure difference over a module resulting from the operation of a fan to be described below cannot result in an intrusive backflow outside the modules.

The construction of a module will be further discussed below with reference to FIGS. 5A and 5B.

Figure 3A:
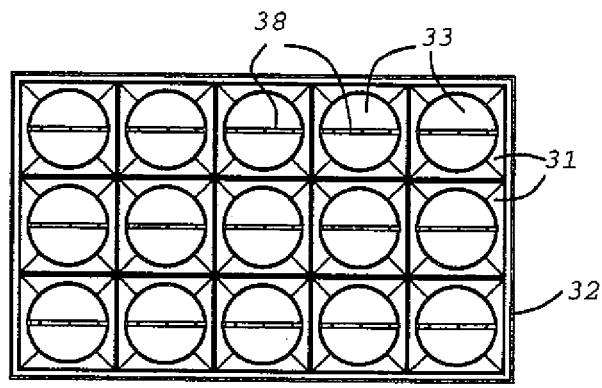
FIG. 3A shows a cross-section through another auxiliary device in which the air conditioning modules are arranged in a 3×5 matrix arrangement.
Figure 3B:
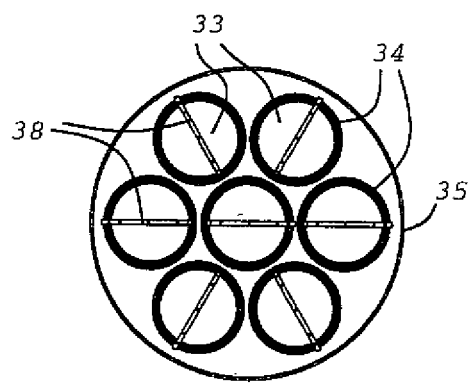
FIG. 3B shows a cross-section through another embodiment in which seven modules are accommodated in a round housing.
Figure 3C:
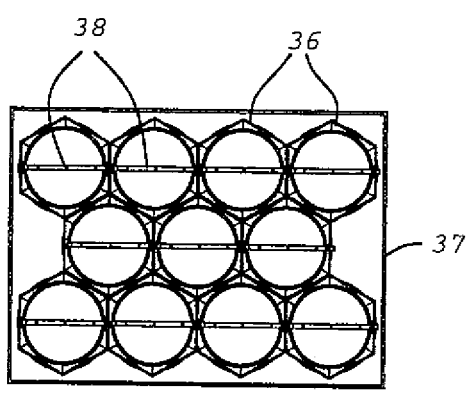
FIG. 3C shows an alternative arrangement in which the outer form of the modules is embodied in part as a regular hexagon, and in which the modules are disposed in three rows of respectively four, three and four modules.

FIGS. 3A, 3B and 3C show by way of example cross-sections of three other possible patterns in which modules can be ordered.

The modules according to FIG. 3A, which are all designated 31, have a rectangular cross-section locally and are accommodated in a pattern in a housing 32. Reference numeral 33 designates valves, each with a valve axis 38, which correspond with valves 21 and 22 according to FIG. 2A.

FIG. 3B shows that modules 34 can have a round outer form and can be accommodated in a cylindrical housing 35.

FIG. 3C shows a regular hexagonal form of the outer side of modules 36, which in this embodiment are accommodated in a housing 37 of rectangular cross-section. It is noted that modules 36 could also be used for the pattern according to FIG. 3B, which has a six-fold symmetry.

Figure 4:
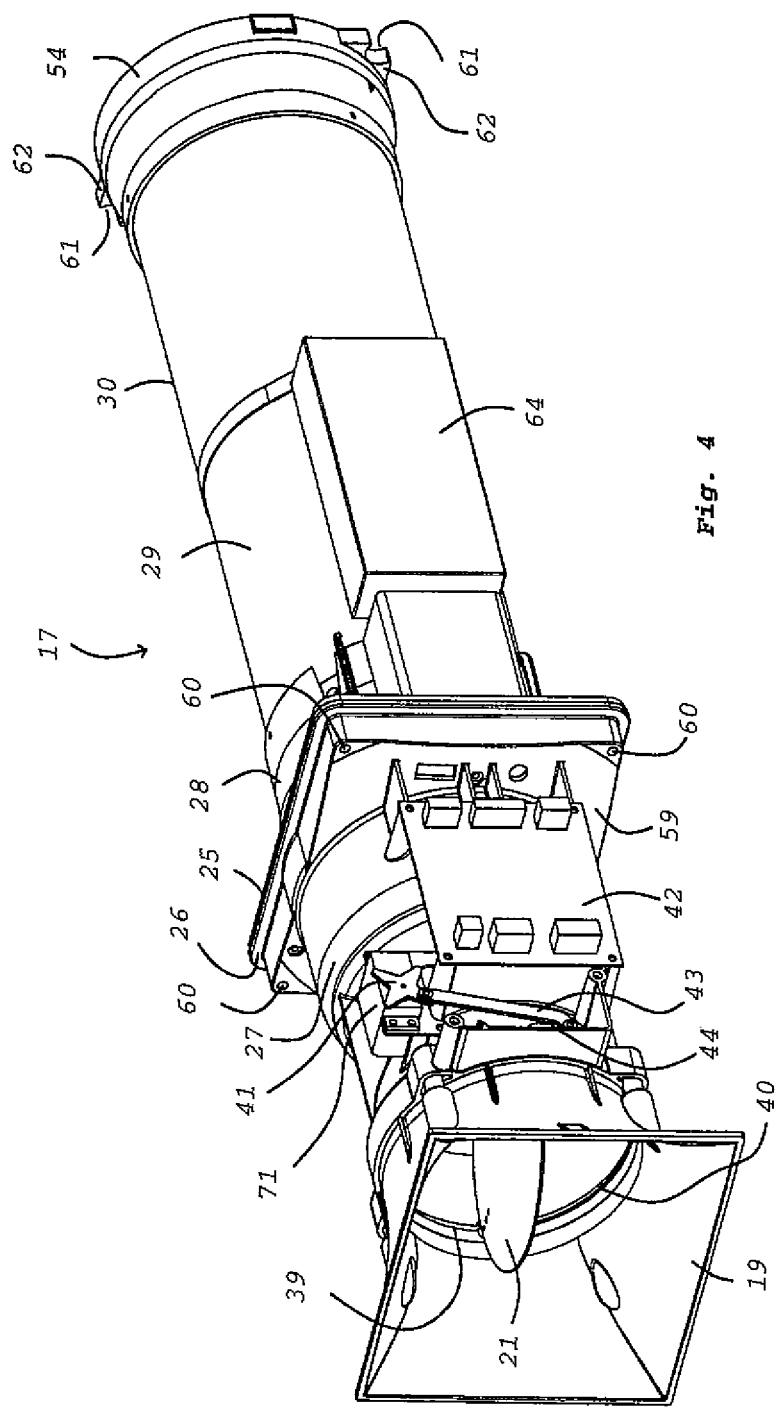
FIG. 4 is a perspective view of an air conditioning module as applied in the auxiliary device according to FIG. 2A.

FIG. 4 shows a perspective view of module 17.

It can be clearly seen that valve 21, by being rotated from its drawn open position to its closed position (compare the closed valve 22 shown in FIG. 2) by rotation around the valve axis 38 (see FIG. 3), moves into sealing co-action with two semicircular sealing ring parts 39, 40 (see also FIG. 5A). An electrical actuator 71 provides for rotation of a drive wheel 41 under the control of an individual module control unit 42 which, just as comparable units of other modules, is or can be connected to a central control unit. By means of a lever 43 the valve shaft 28 is rotated in otherwise known manner by means of a second drive wheel 44 or drive arm while co-displacing the valve 21, whereby this latter can be displaced between the opened and the closed position under said control.

As can be seen clearly in FIGS. 2A and 5A, module 17 further comprises a fan comprising a motor 45 and a rotor 46. This wheel comprises a number of blades 49 which are placed angularly equidistantly and the inner edges 47 of which lie substantially on an imaginary cylinder, while outer edges 48 lie at least more less on an imaginary truncated cone, or have a certain curvature relative to this main form, or taper toward a direction of the flow. This structure ensures a good output in terms of the pressure difference between the inlet and the outlet of module 17, causes little noise production and is able to produce a flow rate which is high compared to for instance axial fans, expressed in the quantity of air pumped per unit of time. Nor is a standard tangential fan capable of this combined performance.

The upper part of housing 30 has on its inner side a high measure of diffuse reflection for UV(C) radiation. The inner surface of part 29 can for instance be provided for this purpose with a coating consisting of sputtered aluminum. In the space enclosed by this reflective cylindrical wall, the UV treatment chamber 50, is situated a UV source of two UV lamps 51, 52. These lamps generate, among other things, strong UV(C) radiation at a wavelength of 253.7 nm which, as is known, has a strong microorganism-killing effect. The lamps are of per se known and generally usual type. They are inserted into a plug-in unit 53 and are powered via a power supply unit 64 (see FIG. 4). This power supply unit is controlled from the module control unit 42. In this manner the lamps can be controlled by the electronic control such that the UV(C) radiation emitted by the lamps have an optimal intensity within certain tolerances. For this purpose the motor 45 of fan 45, 46 is also controlled such that the lamps are operated as far as possible at a temperature at which the intensity of the emitted UV(C) radiation is as high as possible. For most lamps this temperature is in the order of 40° C. The temperature also depends on the speed of the flow-by air. For determined types of lamp this air can preferably have a speed of about 1.5 m/s. This imposes limitations on the possibilities of varying the flow rate of auxiliary device 1. It is now precisely the modular structure which makes it possible to vary the output of the device within the wide limits while retaining an optimal choice within narrow limits of the values of the relevant parameters.

Figure 5B:
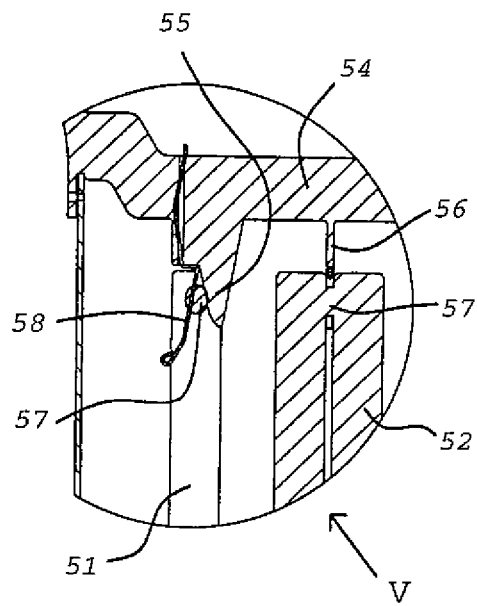
FIG. 5B shows the detail V of FIG. 5A.
Figure 5A:
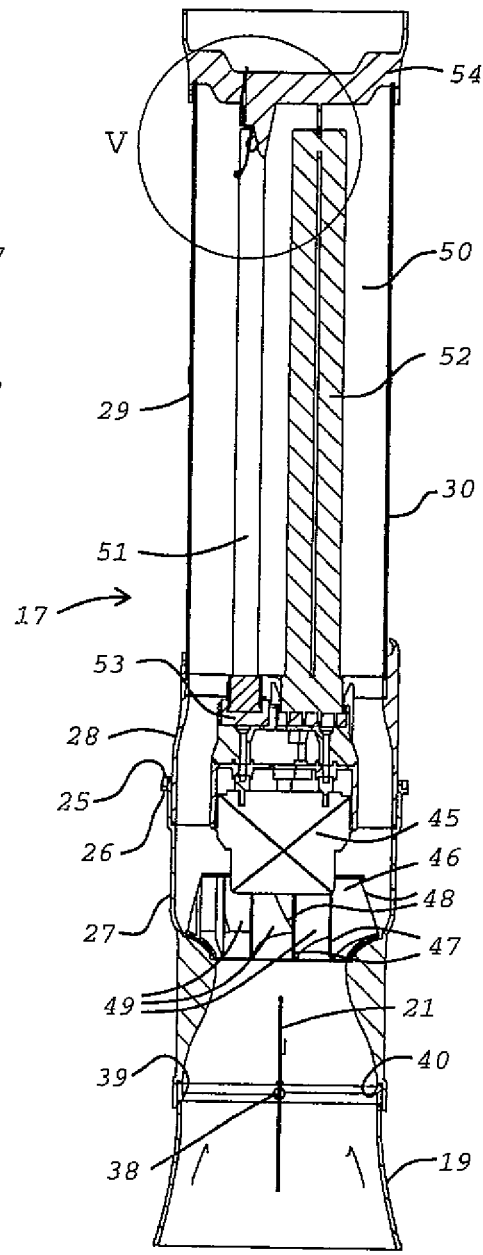
FIG. 5A shows a longitudinal section through the air conditioning module according to FIG. 4.

The detail V in FIG. 5B shows that the upper part of housing 30 is covered with a fixation ring 54 which serves to fix the lamps 51, 52. Ring 54 comprises for this purpose protrusions 55, 56 which engage on the transition zone 57 between the vertical legs of lamps 51, 52 while a clamping spring 58 consisting of steel wire provides for a pressure contact between this zone 57 and the associated protrusion 55, 56.

Figure 6:
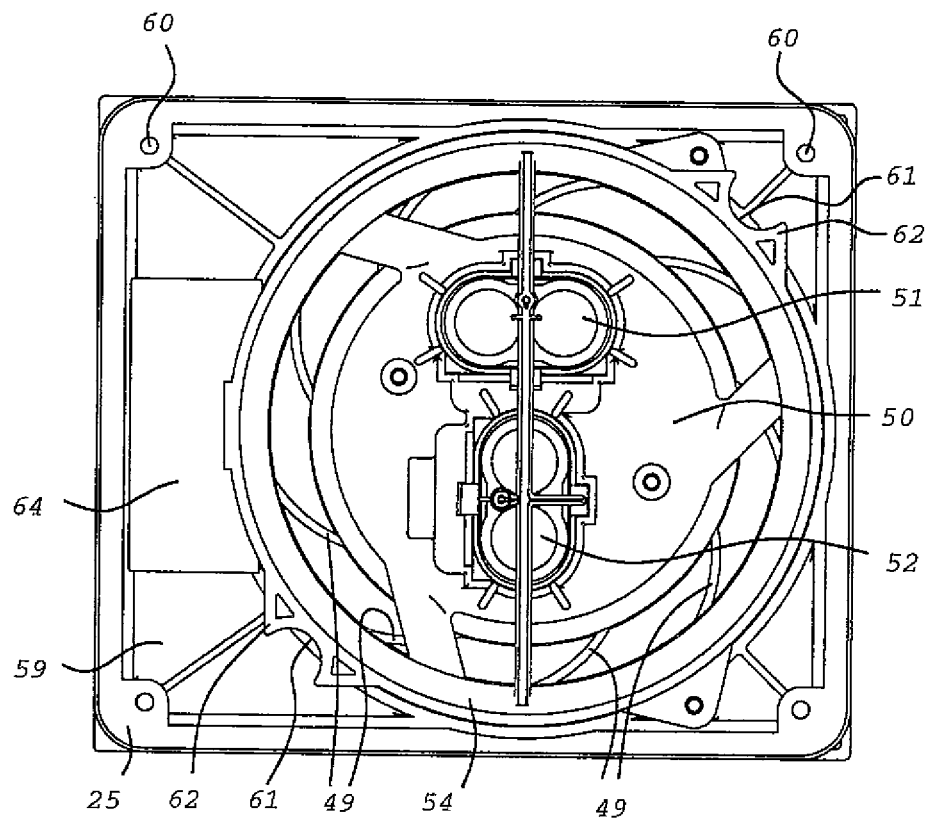
FIG. 6 is a top view of the air conditioning module according to FIGS. 4 and 5 with the omission of the end cover.

FIG. 6 further shows that a rectangular support edge 59 is arranged on the lower part 27 of housing 30. This supports sealing ring 25. Four continuous holes 60 are arranged herein for the purpose of fastening to sealing profile 24 by means of screws.

In respect of the arrangement of lamps 51, 52 it is noted that, as can be seen particularly clearly in FIG. 6, they can be rotated 90° relative to each other. This arrangement ensures the highest possible average intensity of the UV radiation in UV treatment chamber 50.

Referring to FIG. 4, attention is further drawn to two protrusions 62 lying diagonally opposite each other and each provided with a semicircular recess 61. Not drawn in the figures is that during sliding of a module into housing 11 these recesses 61 co-act in rotation-locking manner with guide rods present in housing 11 which ensure correct positioning of module 17 on its front side. On the rear side the correct positioning is provided by support edge 59 with the continuous holes 60, by means of which the fixation of module 17 in housing 11 can be ensured.

Figure 7B:
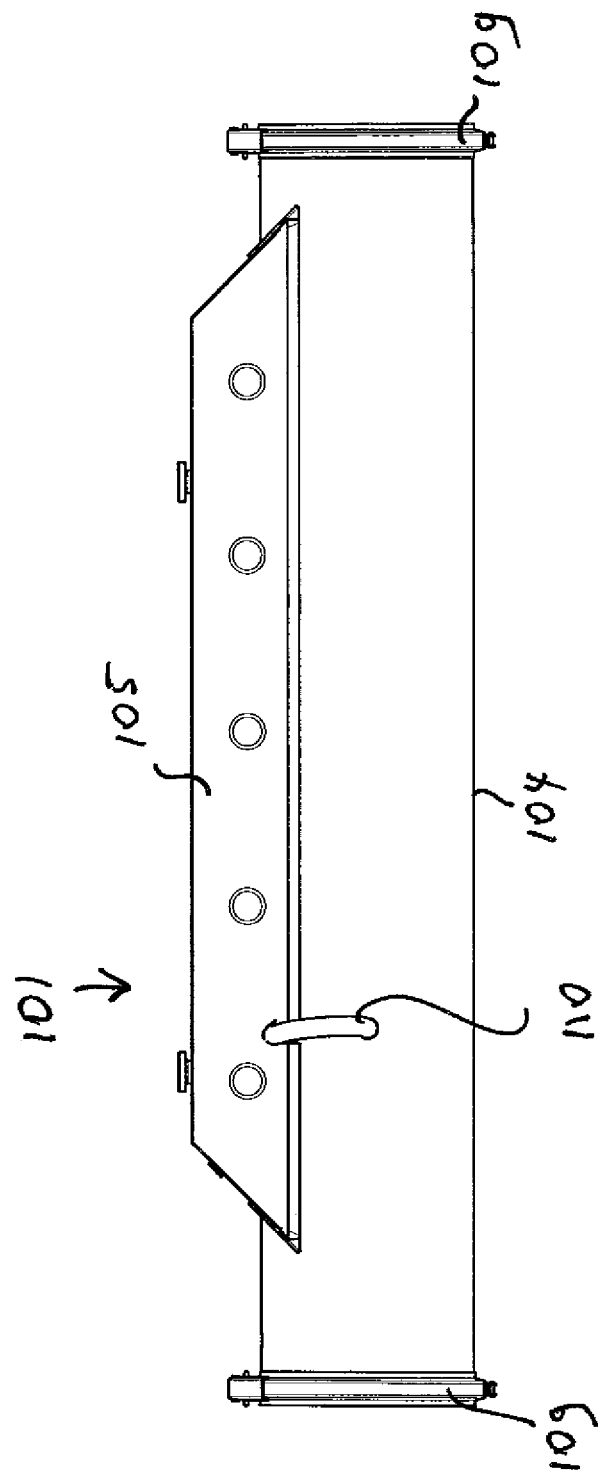
FIG. 7B is a side view of the air conditioning module according to FIG. 7A.

FIG. 7A shows an air conditioning module adapted to sterilize air in a UV treatment chamber in which an elongate UV lamp is accommodated.

Module 101 comprises a tube 104 which has on its ends flanges for modular coupling to other modules and/or connection to an air conduit. Use is made for this purpose of a Jacobs clamp, i.e. a divisible ring 109, as will be further elucidated with reference to FIGS. 8, 9, 10 and 11.

Figure 7D:
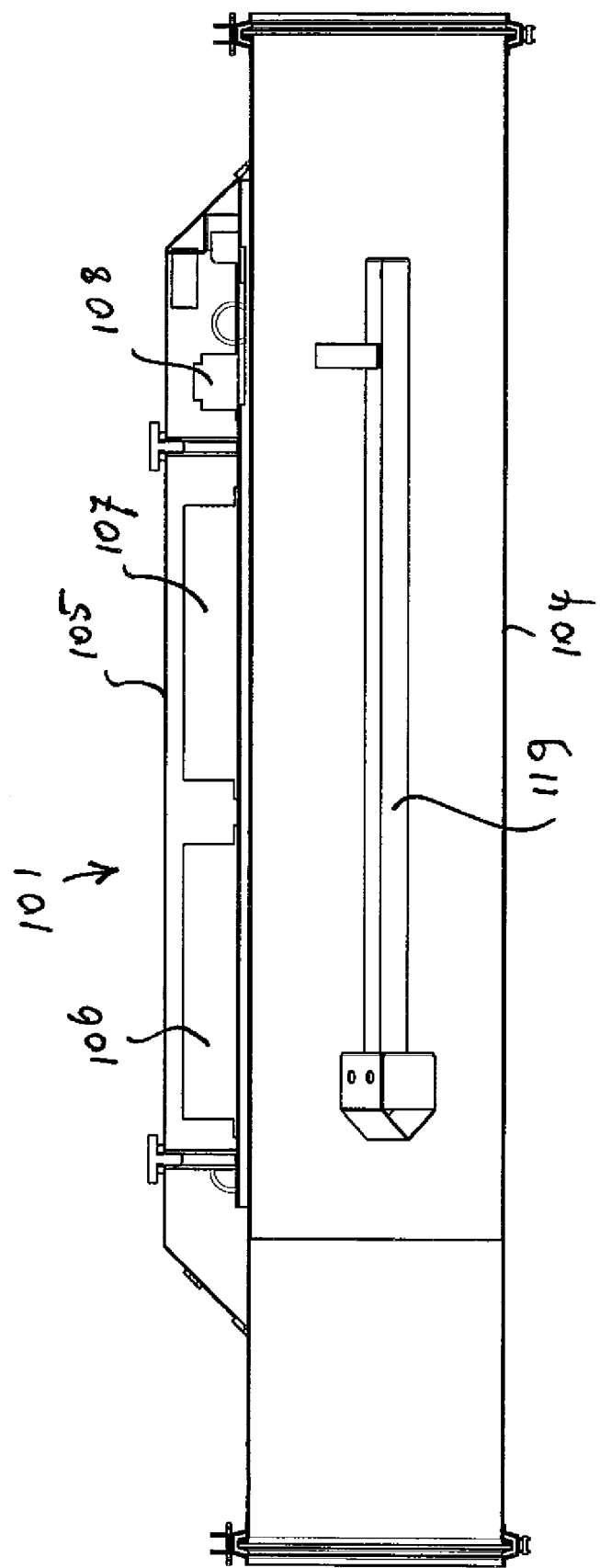
FIG. 7D is a side view as according to FIG. 7C.

Tube 104 carries a releasable cover 105 accommodating chokes 106, 107 and electronic units 108. See FIG. 7C herefor. In this embodiment of the chokes are connected to UV lamp 119 by means of a cable 110 extending outside tube 104 and cover 105, see FIG. 7D.

The Jacobs clamps are designated with reference numeral 109.

FIG. 8 shows the modular coupling between an air conditioning module 101 and a fan module 102.

FIG. 8C shows that the fan comprises a motor 111 and blades 112.

This is an appropriate moment to note that UV lamp 113, which is situated in the tube 104 serving as UV treatment chamber, a radiates the inner wall of this tube 104. This latter is preferably diffusely reflective with a high reflection coefficient. In this embodiment the whole inner surface of tube 104 takes a diffusely reflective form. Use is made of a coating of $TiO_2$. The surfaces of the fan, including blades 112, which are irradiated by UV radiation are also provided with a $TiO_2$ coating. It is important that the diffusely reflecting layer extends over a distance which is considerably greater than the physical length of lamp 113. This is the reason why the whole inner surface is provided with such a layer. It due to the relatively great length of the diffusely reflecting layer the efficiency of the air conditioning device, i.e. elimination of harmful micro organisms, is greatly improved.

Figure 9C:
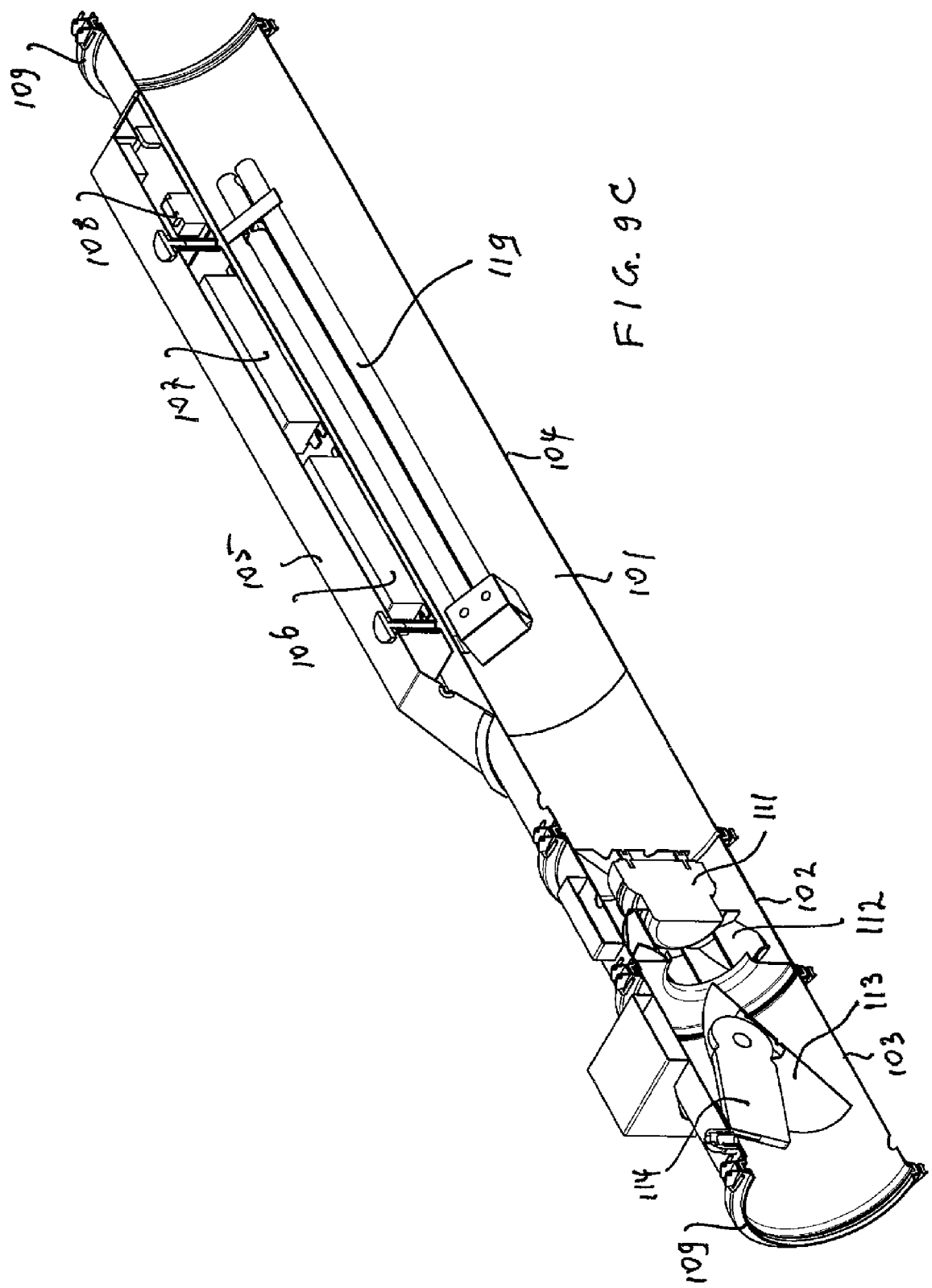
FIG. 9C is a view corresponding with FIG. 7D of the modular unit of FIG. 9A.

FIG. 9 shows the modular coupling of air conditioning module 101, a fan module 102 and a valve module 103. As will be particularly apparent from FIG. 9D, the valve body is displaceable between an opened position, in which it provides a negligible flow resistance, and a close position in which it for the closes the passage of valve module 103. The drive of valve body 113 is designated with reference numeral 114.

Figure 10:
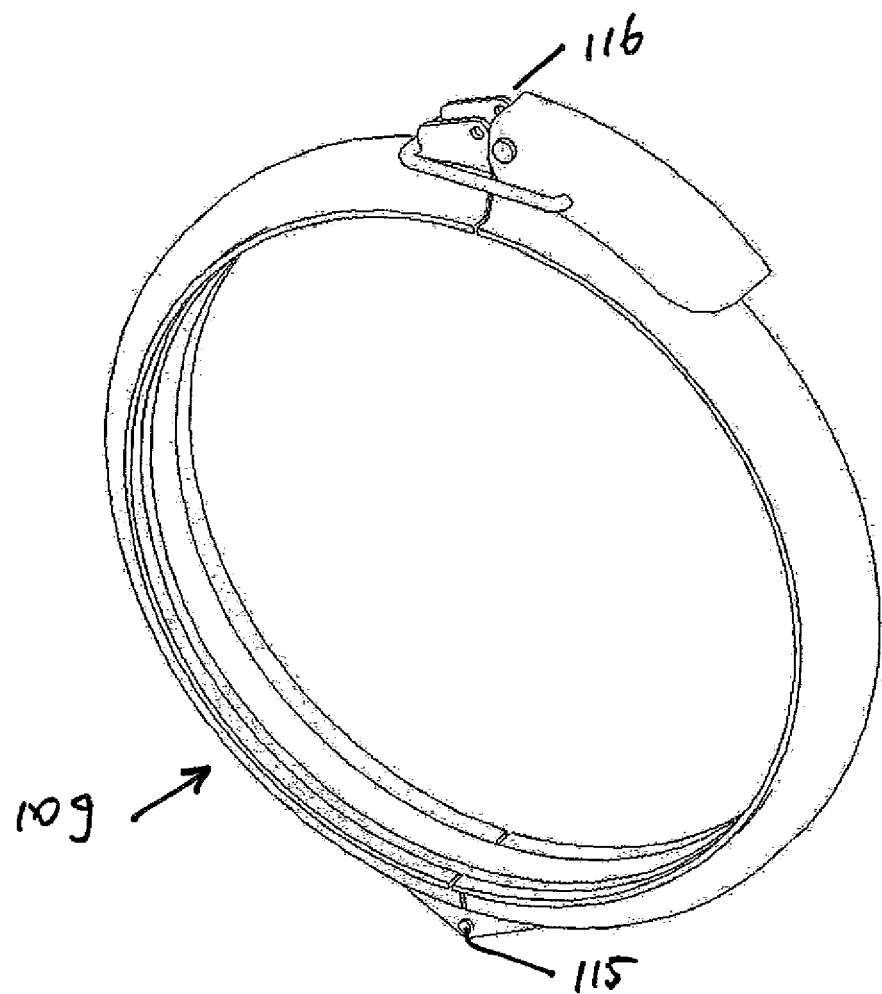
FIG. 10 shows a divisible ring, a so-called "Jacobs clamp"

FIG. 10 shows the Jacobs clamp 109 on larger scale. It will be apparent that it has been drilled out as a divided ring, the two semicircular parts of which are mutually connected with a hinge connection 115. Situated on the top is a known clamp 116 with which the divided ring 109 can be closed in order to couple the modules in the manner shown as examples in FIGS. 7, 8 and 9.

Figure 11:
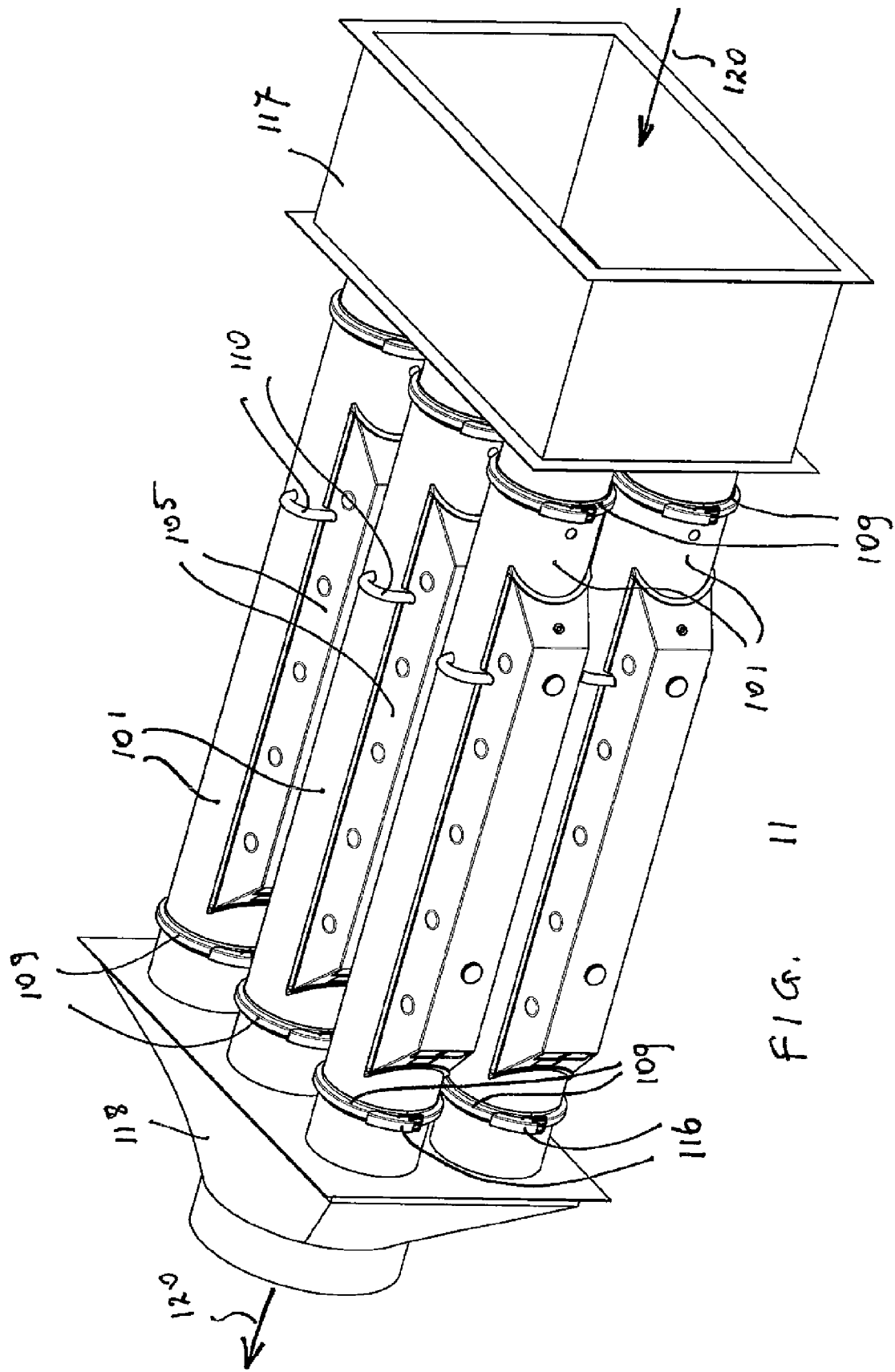
FIG. 11 shows an auxiliary device according to the invention comprising a number of modular units as according to FIG. 7.

FIG. 11 finally shows that by means of an inlet manifold 117 and an outlet manifold 118 six air treatment modules 101 are coupled in mutually parallel relation by means of Jacobs clamps 109 such that the modules 101 active at any moment allow passage of the whole airflow 120.

It is noted that, for the sake of overall clarity in the drawings, power supply and signal cables with which electronic units 108 control fan module 102 and/or valve module 103 are not shown.

Attention is emphatically drawn to the fact that the shown and described exemplary embodiments all relate to air conditioning modules which are adapted to filter air by means of a filter unit and to eliminate micro-organisms by subjecting air flowing through the modules for a period of time to UV(C) radiation of a certain minimum intensity. The invention is not however limited to such an application. The auxiliary devices according to the invention can also fulfil other than the stated functions. Such functions are stated in the above specification.

Attention is also drawn to the fact that more than one auxiliary device according to the invention can be accommodated in one air conduit. Two functionally equivalent auxiliary devices can for instance together achieve that a sought value of a quantity lies below or above a set threshold value. Different auxiliary devices can also have differing functions, for instance filtering and drying, cooling and disinfecting and so forth.

The invention claimed is:
1. An auxiliary device in an air conduit,
    said air conduit extending between a first air feed and a first air discharge, forming part of an air conditioning device and wherein a whole main airflow flows through said auxiliary device,
    said auxiliary device having a modular structure comprising a housing, said housing comprising an arrangement of a plurality of air conditioning modules, each of the plurality of air conditioning modules being directly adjacent another one of the plurality of air conditioning modules, said air conditioning modules are substantially identical and, in an active state, each air conditioning module allows passage of a partial flow of the whole main airflow, wherein the whole main airflow rate is a sum of the partial airflow rates passing through the active modules, and together the plurality of air conditioning modules allow passage of the whole main airflow through the first air discharge at a common outlet;
    said auxiliary device further comprising a feed part and a discharge part connected to air conduit first flow components, said first flow components produce a variable main airflow through the air conduit; and
    at least one control unit configured to individually transition each of the air conditioning modules between an active state, wherein passage of the partial flow is allowed, and a passive state, wherein the partial flow substantially amounts to zero or flows in an opposite direction of a whole main airflow direction;

wherein each of said air conditioning modules comprises at least one valve, wherein each of said at least one valve is controlled by the at least one control unit, and each of said at least one valve operates between an open and a closed position, wherein the at least one valve provides a predetermined partial airflow rate for the active air conditioning module, and all valves provide a same predetermined partial airflow rate in all active air conditioning modules to meet a desired air conditioning system main airflow rate; and wherein the desired air conditioning system main airflow rate varies over time and wherein the control unit is configured to vary the number of active air conditioning modules during operation of the air conditioning system, thereby adjusting the sum of all partial airflow rates of the air conditioning modules to the desired air conditioning system main airflow rate every time said air conditioning system main airflow rate changes.

2. The auxiliary device as claimed in claim 1, wherein:
each air conditioning module comprises:
a housing with an air feed and an air discharge; and
a UV treatment chamber which is received in the housing and through which the entire partial flow flows, wherein a UV radiation source is accommodated for the purpose of exposing the partial flow to UV radiation in order to kill micro-organisms present in the partial flow.

3. The auxiliary device as claimed in claim 2, wherein:
in case the UV radiation source breaks down, the at least one control unit being adapted to take an air conditioning module from the active state to the passive state.

4. The auxiliary device as claimed in claim 2, further comprising:
adjusting components for adjusting the UV radiation source such that the intensity of the UV radiation is in an operating range of the source and differs from a maximum intensity by less than 10%.

5. The auxiliary device as claimed in claim 4, wherein the adjusting components are further adapted to modify a speed of the air flow along the UV radiation source.

6. The auxiliary device as claimed in claim 5, further comprising temperature measuring components adapted to measure the difference between an output temperature and an input temperature of the UV treatment chamber and to control the adjusting components.

7. The auxiliary device as claimed in claim 5, further comprising intensity measuring components adapted to measure the intensity of the UV radiation emitted by the UV radiation source and to control the adjusting components.

8. The auxiliary device as claimed in claim 2, wherein at least a part of a surface irradiated by UV radiation is provided with a photo catalytic oxidation coating.

9. The auxiliary device as claimed in claim 8, wherein the device comprises a fan having blades wherein at least a surface of the fan irradiated by UV radiation is provided with a photo catalytic oxidation coating.

10. The auxiliary device as claimed in claim 2, wherein an inner wall of the UV treatment chamber is provided with a reflective coating which is situated in a region of the UV source and extends further upstream and downstream over a distance at least equal to 40% of a length of the UV radiation source in a lengthwise direction of the UV treatment chamber.

11. The auxiliary device as claimed in claim 10, wherein the coating is diffusely reflective.

12. The auxiliary device as claimed in claim 1, wherein:
second flow components controlled by the at least one control unit are accommodated in each air conditioning module, said at least one control unit being adapted to transition the partial flow to a desired positive, zero or negative value.

13. The auxiliary device as claimed in claim 12, wherein:
in case the second flow components break down, the at least one control unit being further adapted to transition an air conditioning module from the active state to the passive state.

14. The auxiliary device as claimed in claim 12, further comprising:
pressure drop measuring components adapted to measure the pressure drop over each air conditioning module and to generate output signals to the at least one control unit; and
the at least one control unit being adapted to control the second flow components by the output signals received such that the pressure drop over each air conditioning module substantially amounts to zero.

15. The auxiliary device as claimed in claim 12, wherein:
the second flow components comprise a fan having angularly equidistant blades disposed on a rotor defining a rotational axis, inner edges of the blades are parallel to the rotational axis and outer edges of the blades are inclined relative to the axis of rotation, these outer edges forming together with a substantially cylindrical envelope a free space widening in the direction of the whole main airflow.

16. The auxiliary device as claimed in claim 1,
the at least one control unit being further adapted to record the cumulative active time duration of each air conditioning module, and being further adapted to switch the individual modules on and off, wherein each of the air conditioning modules are configured to have a substantially equal cumulative active time duration.

17. The auxiliary device as claimed in claim 1, wherein:
the inner dimensions of a housing of the auxiliary device are chosen in combination with the outer form of the air conditioning modules such that the air conditioning modules can be accommodated fitting into the housing in a substantially closest stacking.

18. The auxiliary device as claimed in claim 1, also comprising at least one separate fan module and at least one separate valve module, wherein each air conditioning module, each fan module and each valve module is sealingly coupled to each other in pairs in any desired arrangement, wherein all modules comprise substantially same flanges, and flanges placed against each other are coupled releasably to each other by a divisible and closable ring, which in close position extends over both flanges and holds these flanges pressed against each other, such that the modules can be mutually coupled in modular manner in all desired numbers and in any desired arrangement.

19. The auxiliary device as claimed in claim 18, wherein a valve module is placed at both an inlet side and an outlet side of the air conditioning module such that after closure of the valves of the two valve modules the air conditioning module can be removed.

20. An air conditioning device, comprising:
an auxiliary device as claimed in claim 1.

21. The auxiliary device as claimed in claim 1, wherein the at least one control unit comprises a central processor which controls each of the air conditioning modules.

* * * * *